US012657708B2

(12) United States Patent　　(10) Patent No.:　US 12,657,708 B2
Ihara　　(45) Date of Patent:　Jun. 16, 2026

(54) IMAGE PROCESSING APPARATUS, METHOD FOR OPERATING IMAGE PROCESSING APPARATUS, AND PROGRAM FOR OPERATING IMAGE PROCESSING APPARATUS

(71) Applicant: FUJIFILM Corporation, Tokyo (JP)

(72) Inventor: Satoshi Ihara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 433 days.

(21) Appl. No.: 18/453,320

(22) Filed: Aug. 22, 2023

(65) Prior Publication Data

US 2023/0394661 A1　　Dec. 7, 2023

Related U.S. Application Data

(63) Continuation of application No. PCT/JP2021/045208, filed on Dec. 8, 2021.

(30) Foreign Application Priority Data

Mar. 3, 2021　　(JP) ................................. 2021-033847

(51) Int. Cl.
　　*G06T 7/00*　　(2017.01)
　　*A61B 6/03*　　(2006.01)
　　　　　　(Continued)
(52) U.S. Cl.
　　CPC ............ *G06T 7/0012* (2013.01); *A61B 6/032* (2013.01); *A61B 6/505* (2013.01); *G06T 7/11* (2017.01);
　　　　　　(Continued)
(58) Field of Classification Search
　　CPC . G06T 7/0012; G06T 7/11; G06T 7/70; G06T 2207/10081; G06T 2207/20081;
　　　　　　(Continued)

(56) References Cited

U.S. PATENT DOCUMENTS 9,401,020　B1　7/2016　Li et al.
2009/0285466　A1 *　11/2009　Hipp ..................... G06T 7/0014
　　　　　　　　　　　　　　382/131

(Continued)

FOREIGN PATENT DOCUMENTS

JP　　2007088831　　4/2007
JP　　2009163661　　7/2009

(Continued)

OTHER PUBLICATIONS

"International Search Report (Form PCT/ISA/210) of PCT/JP2021/ 045208," mailed on Feb. 22, 2022, with English translation thereof, pp. 1-5.

(Continued)

*Primary Examiner* — Jennifer Mehmood
*Assistant Examiner* — Jose M Torres
(74) *Attorney, Agent, or Firm* — JCIPRNET

(57) ABSTRACT

An image processing apparatus comprising: a processor and a memory connected to or incorporated in the processor, in which the processor acquires an analysis target image in which a plurality of contiguous target objects of the same type appear, receives an input of a marker indicating positions of the target objects in the analysis target image, generates a marker position display map indicating a position of the marker in the analysis target image, inputs the analysis target image and the marker position display map to a semantic segmentation model, and outputs, from the semantic segmentation model, an output image in which the target objects are identified.

10 Claims, 29 Drawing Sheets

(51) Int. Cl.

| | |
|---|---|
| *A61B 6/50* | (2024.01) |
| *G06T 7/11* | (2017.01) |
| *G06T 7/70* | (2017.01) |
| *G06V 10/25* | (2022.01) |
| *G06V 20/64* | (2022.01) |
| *G16H 30/20* | (2018.01) |
| *G16H 30/40* | (2018.01) |
| *G16H 40/63* | (2018.01) |
| *G16H 50/20* | (2018.01) |

(52) U.S. Cl.
CPC ................ *G06T 7/70* (2017.01); *G06V 10/25* (2022.01); *G06V 20/653* (2022.01); *G16H 30/20* (2018.01); *G16H 30/40* (2018.01); *G16H 40/63* (2018.01); *G16H 50/20* (2018.01); *G06T 2207/10081* (2013.01); *G06T 2207/20081* (2013.01); *G06T 2207/30012* (2013.01); *G06T 2207/30204* (2013.01)

(58) Field of Classification Search
CPC ........... G06T 2207/30012; G06T 2207/30204; G16H 30/20; G16H 30/40; G16H 40/63; G16H 50/20; A61B 6/032; A61B 6/505; G06V 10/25; G06V 20/653
See application file for complete search history.

(56) References Cited

U.S. PATENT DOCUMENTS

2015/0003695 A1 1/2015 Ayed et al.

| | | | | |
|---|---|---|---|---|
| 2020/0082221 | A1* | 3/2020 | Tsai | G06T 7/11 |
| 2020/0129243 | A1 | 4/2020 | Kemp et al. | |
| 2020/0364856 | A1* | 11/2020 | Nicolaes | G06T 15/08 |
| 2021/0133979 | A1 | 5/2021 | Takahashi | |
| 2021/0378616 | A1* | 12/2021 | Chan | A61B 6/032 |
| 2021/0383565 | A1* | 12/2021 | Le | G06N 3/09 |
| 2022/0028076 | A1* | 1/2022 | Masuzawa | G06T 7/11 |
| 2022/0114393 | A1* | 4/2022 | Keshwani | G06N 3/08 |
| 2022/0172350 | A1* | 6/2022 | Miao | G06V 20/647 |
| 2022/0207722 | A1* | 6/2022 | Kim | G06T 7/0012 |
| 2022/0215201 | A1* | 7/2022 | Dwivedi | G06V 10/764 |
| 2022/0327732 | A1 | 10/2022 | Shimauchi | |
| 2023/0034101 | A1* | 2/2023 | Yardibi | A61B 34/25 |

FOREIGN PATENT DOCUMENTS

| | | |
|---|---|---|
| JP | 2020025730 | 2/2020 |
| JP | 2021033573 | 3/2021 |
| WO | 2013015381 | 1/2013 |

OTHER PUBLICATIONS

"Written Opinion of the International Searching Authority (Form PCT/ISA/237) of PCT/ JP2021/045208," mailed on Feb. 22, 2022, with English translation thereof, pp. 1-8.
"Notice of Reasons for Refusal of Japan Counterpart Application", issued on Sep. 9, 2025, with English translation thereof, pp. 1-6.
"Notice of Reasons for Refusal of Japan Counterpart Application", issued on Feb. 3, 2026, with English translation thereof, p. 1-p. 4.

* cited by examiner

No.1 | ELEMENT VALUE: 1 | LABEL: A
No.2 | ELEMENT VALUE: 2 | LABEL: B
No.3 | ELEMENT VALUE: 3 | LABEL: C
No.4 | ELEMENT VALUE: 1 | LABEL: A
No.5 | ELEMENT VALUE: 2 | LABEL: B
No.6 | ELEMENT VALUE: 3 | LABEL: C
No.7 | ELEMENT VALUE: 1 | LABEL: A
No.8 | ELEMENT VALUE: 2 | LABEL: B
No.9 | ELEMENT VALUE: 3 | LABEL: C
OTHER THAN MARKERS | ELEMENT VALUE: 0

51_1,3,5,7,9          51_2,4,6,8

(PRESENCE PROBABILITY, ABSENCE PROBABILITY)

Figure 31:
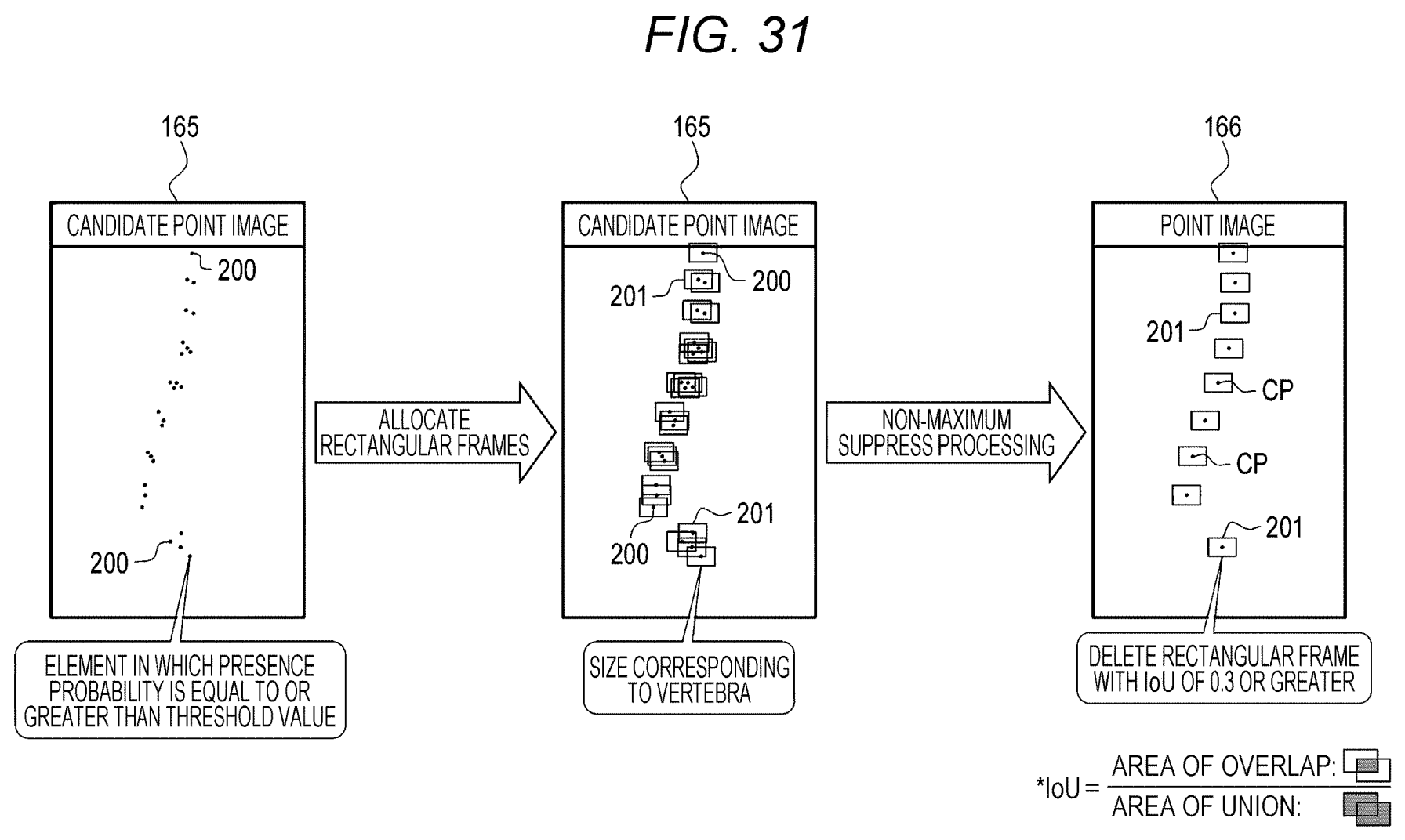

POINT IMAGE

CP

CP

201

201

DELETE RECTANGULAR FRAME
WITH IoU OF 0.3 OR GREATER

*IoU = $\dfrac{\text{AREA OF OVERLAP:}}{\text{AREA OF UNION:}}$

NON-MAXIMUM
SUPPRESS PROCESSING

165

CANDIDATE POINT IMAGE

200

201

201

200

SIZE CORRESPONDING
TO VERTEBRA

ALLOCATE
RECTANGULAR FRAMES

165

CANDIDATE POINT IMAGE

200

200

ELEMENT IN WHICH PRESENCE
PROBABILITY IS EQUAL TO OR
GREATER THAN THRESHOLD VALUE

IMAGE PROCESSING APPARATUS, METHOD FOR OPERATING IMAGE PROCESSING APPARATUS, AND PROGRAM FOR OPERATING IMAGE PROCESSING APPARATUS

CROSS-REFERENCE TO RELATED APPLICATIONS

This application is a continuation application of International Application No. PCT/JP2021/045208 filed on Dec. 8, 2021, the disclosure of which is incorporated herein by reference in its entirety. Further, this application claims priority from Japanese Patent Application No. 2021-033847 filed on Mar. 3, 2021, the disclosure of which is incorporated herein by reference in its entirety.

BACKGROUND

1. Technical Field

The present invention relates to an image processing apparatus, a method for operating the image processing apparatus, and a program for operating the image processing apparatus.

2. Description of the Related Art

Conventionally, image processing for identifying a target object appearing in an analysis target image has been performed in various fields. In recent years, a method using a convolutional neural network (hereinafter, abbreviated as CNN) that performs semantic segmentation for identifying a target object appearing in an analysis target image in units of pixels has attracted attention. For example, JP2020-025730A describes that a radiographic image obtained by irradiating a patient with radiation is used as an analysis target image and a plurality of target objects appearing in the radiographic image are identified using a CNN. It also describes that examples of the target objects include a lung field, a spine (backbone), and other regions, and that a thoracic vertebra and a lumbar vertebra of the spine are separately identified.

SUMMARY

JP2020-025730A describes that the CNN is used to identify the spine, as described above. However, in practice, the CNN has low accuracy in identifying a plurality of contiguous target objects of the same type, such as each of a plurality of vertebrae constituting the spine. For this reason, there is a case where the identification is not successful, such as a case where a plurality of adjacent vertebrae are erroneously identified as one vertebra.

An embodiment according to the technology of the present disclosure provides an image processing apparatus, a method for operating an image processing apparatus, and a program for operating an image processing apparatus that can increase the accuracy of identification of a plurality of contiguous target objects of the same type.

According to a first aspect of the present disclosure, an image processing apparatus comprises a processor and a memory connected to or incorporated in the processor, in which the processor acquires an analysis target image in which a plurality of contiguous target objects of the same type appear, receives an input of a marker indicating positions of the target objects in the analysis target image, generates a marker position display map indicating a position of the marker in the analysis target image, inputs the analysis target image and the marker position display map to a semantic segmentation model, and outputs, from the semantic segmentation model, an output image in which the target objects are identified.

According to a second aspect of the present disclosure, in the image processing apparatus, the processor generates the marker position display map of the marker corresponding to one of the plurality of contiguous target objects of the same type, and outputs, from the semantic segmentation model, the output image in which the one object is identified.

According to a third aspect of the present disclosure, in the image processing apparatus, the processor generates the marker position display map of the marker corresponding to target objects arranged to face each other with at least one target object interposed therebetween among the plurality of contiguous target objects of the same type, and outputs, from the semantic segmentation model, the output image in which the target objects arranged to face each other with at least one target object interposed therebetween are identified.

According to a fourth aspect of the present disclosure, in the image processing apparatus, the processor generates the marker position display map of the marker corresponding to all of the plurality of contiguous target objects of the same type, and in a case where the marker position display map is generated, the processor attaches a first label to a first target object out of first and second adjacent target objects among the plurality of contiguous target objects of the same type, attaches a second label different from the first label to the second target object, and outputs, from the semantic segmentation model, the output image in which the first target object is identified as a first class corresponding to the first label and the second target object is identified as a second class corresponding to the second label.

According to a fifth aspect of the present disclosure, in the image processing apparatus, the processor combines the analysis target image and the marker position display map in a channel direction in the semantic segmentation model.

According to a sixth aspect of the present disclosure, in the image processing apparatus, in a learning phase, a learning analysis target image and a learning marker position display map are input to the semantic segmentation model, and the semantic segmentation model outputs a learning output image according to the learning analysis target image and the learning marker position display map, and is trained on the basis of comparison between the learning output image and an annotation image which is generated on the basis of the learning analysis target image and in which the target objects to which the marker is attached are annotated.

According to a seventh aspect of the present disclosure, in the image processing apparatus, the analysis target image is a medical image obtained by imaging an inside of a body of a patient, and the target objects are a structure of the body.

According to an eighth aspect of the present disclosure, in the image processing apparatus, the medical image is an image obtained by imaging a spine of the patient, and the structure is a vertebra forming the spine.

According to a ninth aspect of the present disclosure, a method for operating an image processing apparatus comprises: acquiring an analysis target image in which a plurality of contiguous target objects of the same type appear; receiving an input of a marker indicating positions of the target objects in the analysis target image; generating a marker position display map indicating a position of the marker in the analysis target image; inputting the analysis target image and the marker position display map to a semantic segmentation model; and outputting, from the semantic segmentation model, an output image in which the target objects are identified.

According to a tenth aspect of the present disclosure, a program for operating an image processing apparatus causes a computer to execute processing comprising: acquiring an analysis target image in which a plurality of contiguous target objects of the same type appear; receiving an input of a marker indicating positions of the target objects in the analysis target image; generating a marker position display map indicating a position of the marker in the analysis target image; inputting the analysis target image and the marker position display map to a semantic segmentation model; and outputting, from the semantic segmentation model, an output image in which the target objects are identified.

According to the technology of the present disclosure, it is possible to provide an image processing apparatus, a method for operating an image processing apparatus, and a program for operating an image processing apparatus that can increase the accuracy of identification of a plurality of contiguous target objects of the same type.

BRIEF DESCRIPTION OF THE DRAWINGS

Exemplary embodiments according to the technique of the present disclosure will be described in detail based on the following figures, wherein:

FIG. 3 is a block diagram illustrating processing units of a CPU of the diagnosis support apparatus;

FIG. 13 is a diagram illustrating an overview of processing in a learning phase of the semantic segmentation model for target object identification;

FIG. 31 is a diagram illustrating non-maximum suppression processing.

DETAILED DESCRIPTION

First Embodiment

Figure 1:
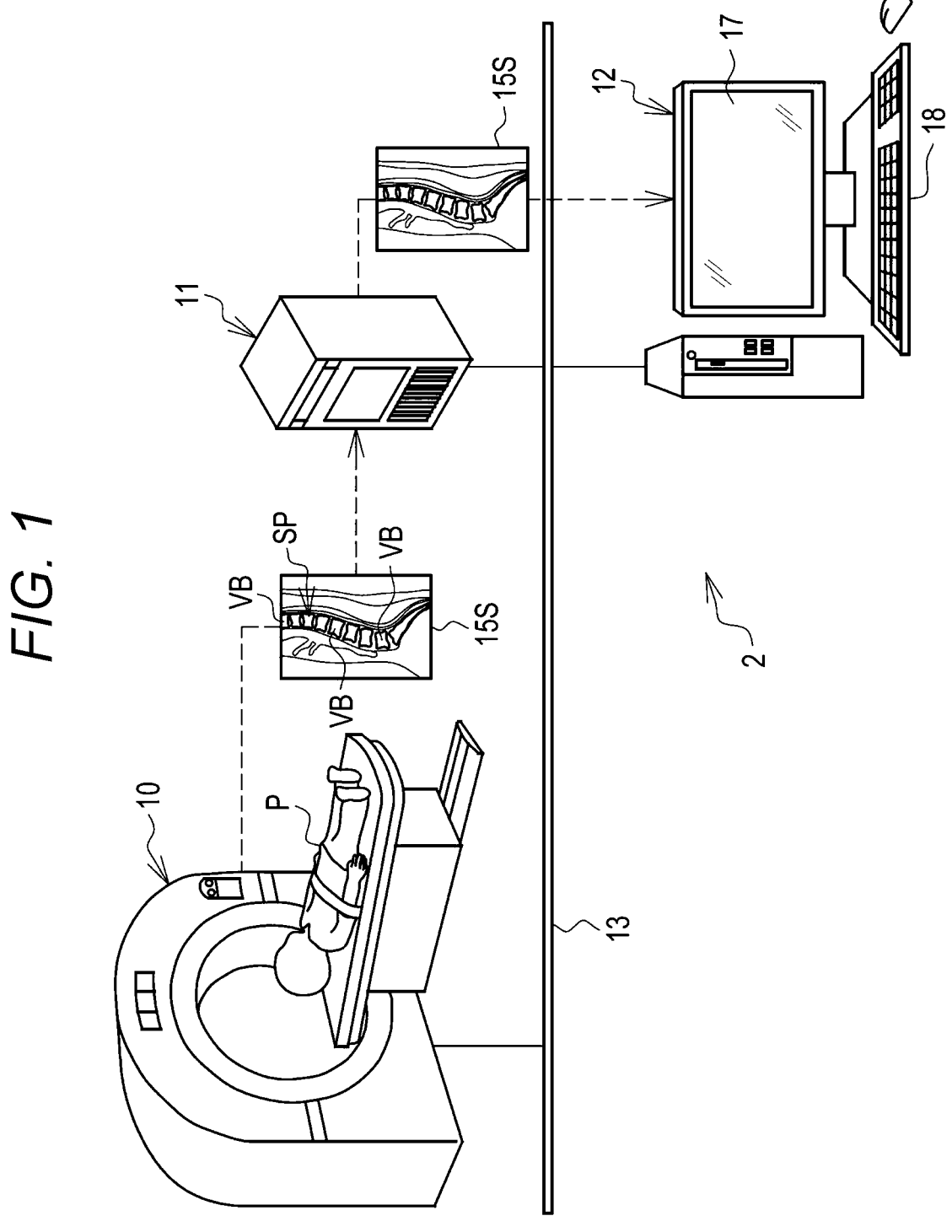
FIG. 1 is a diagram illustrating a medical system including a diagnosis support apparatus.

For example, as illustrated in FIG. 1, a medical system 2 includes a computed tomography (CT) apparatus 10, a picture archiving and communication system (PACS) server 11, and a diagnosis support apparatus 12. The CT apparatus 10, the PACS server 11, and the diagnosis support apparatus 12 are connected to a local area network (LAN) 13 installed in a medical facility, and can communicate with each other via the LAN 13.

As is well known, the CT apparatus 10 performs radiography on a patient P at different projection angles to acquire a plurality of pieces of projection data and reconstructs the acquired plurality of pieces of projection data to output a tomographic image 15 of the patient P. The tomographic image 15 is voxel data indicating a three-dimensional shape of an internal structure of the patient P. In this example, the tomographic image 15 is an image obtained by imaging the upper body of the patient P. FIG. 1 illustrates a tomographic image 15S of a sagittal cross section. A spine SP including a plurality of vertebrae VB appears in the tomographic image 15. The CT apparatus 10 transmits the tomographic image 15 to the PACS server 11. The PACS server 11 stores and manages the tomographic image 15 from the CT apparatus 10. The tomographic image 15 is an example of an "analysis target image" and a "medical image" according to the technology of the present disclosure. In addition, the vertebrae VB are an example of "target objects" and a "structure" of the present disclosure. The reconstruction of the projection data may be performed by the diagnosis support apparatus 12 or the like instead of the CT apparatus 10.

The diagnosis support apparatus 12 is, for example, a desktop personal computer, and is an example of an "image processing apparatus" according to the technology of the present disclosure. The diagnosis support apparatus 12 includes a display 17 and an input device 18. The input device 18 is, for example, a keyboard, a mouse, a touch panel, a microphone, or the like. A doctor operates the input device 18 to transmit a request for distributing the tomographic image 15 of the patient P to the PACS server 11. The PACS server 11 searches for the tomographic image 15 of the patient P that has been requested to be distributed and distributes the tomographic image 15 to the diagnosis support apparatus 12. The diagnosis support apparatus 12 displays the tomographic image 15 distributed from the PACS server 11 on the display 17. The doctor observes the vertebrae VB of the patient P appearing in the tomographic image 15 to diagnose a fracture, metastasis of cancer to bone tissue, and the like. Although FIG. 1 illustrates only one CT apparatus 10 and one diagnosis support apparatus 12, a plurality of CT apparatuses 10 and a plurality of diagnosis support apparatuses 12 may be provided.

Figure 2:
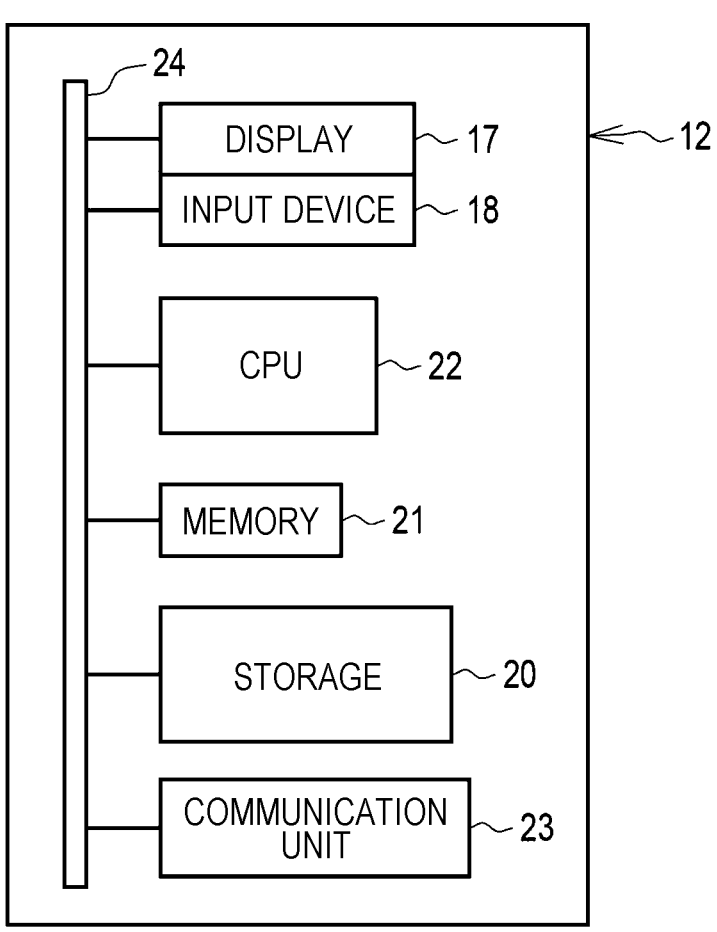
FIG. 2 is a block diagram illustrating a computer constituting the diagnosis support apparatus.

As illustrated in FIG. 2 as an example, the computer constituting the diagnosis support apparatus 12 includes a storage 20, a memory 21, a central processing unit (CPU) 22, and a communication unit 23, in addition to the display 17 and the input device 18 described above. These units are connected to each other via a bus line 24. Note that the CPU 22 is an example of a "processor" according to the technology of the present disclosure.

The storage 20 includes hard disk drives that are built in the computer constituting the diagnosis support apparatus 12 or that are connected to the computer through a cable or a network. Alternatively, the storage 20 is a disk array in which the plurality of hard-disk drives are connected. The storage 20 stores a control program such as an operating system, various application programs, various data associated with these programs, and the like. In addition, a solid state drive may be used instead of the hard-disk drives.

The memory 21 is a working memory for the CPU 22 to execute processing. The CPU 22 loads a program stored in the storage 20 into the memory 21 and executes processing according to the program. Thus, the CPU 22 comprehensively controls the each unit of the computer. The communication unit 23 controls transmission of various kinds of information with an external device such as the PACS server 11. The memory 21 may be built in the CPU 22.

Figure 3:
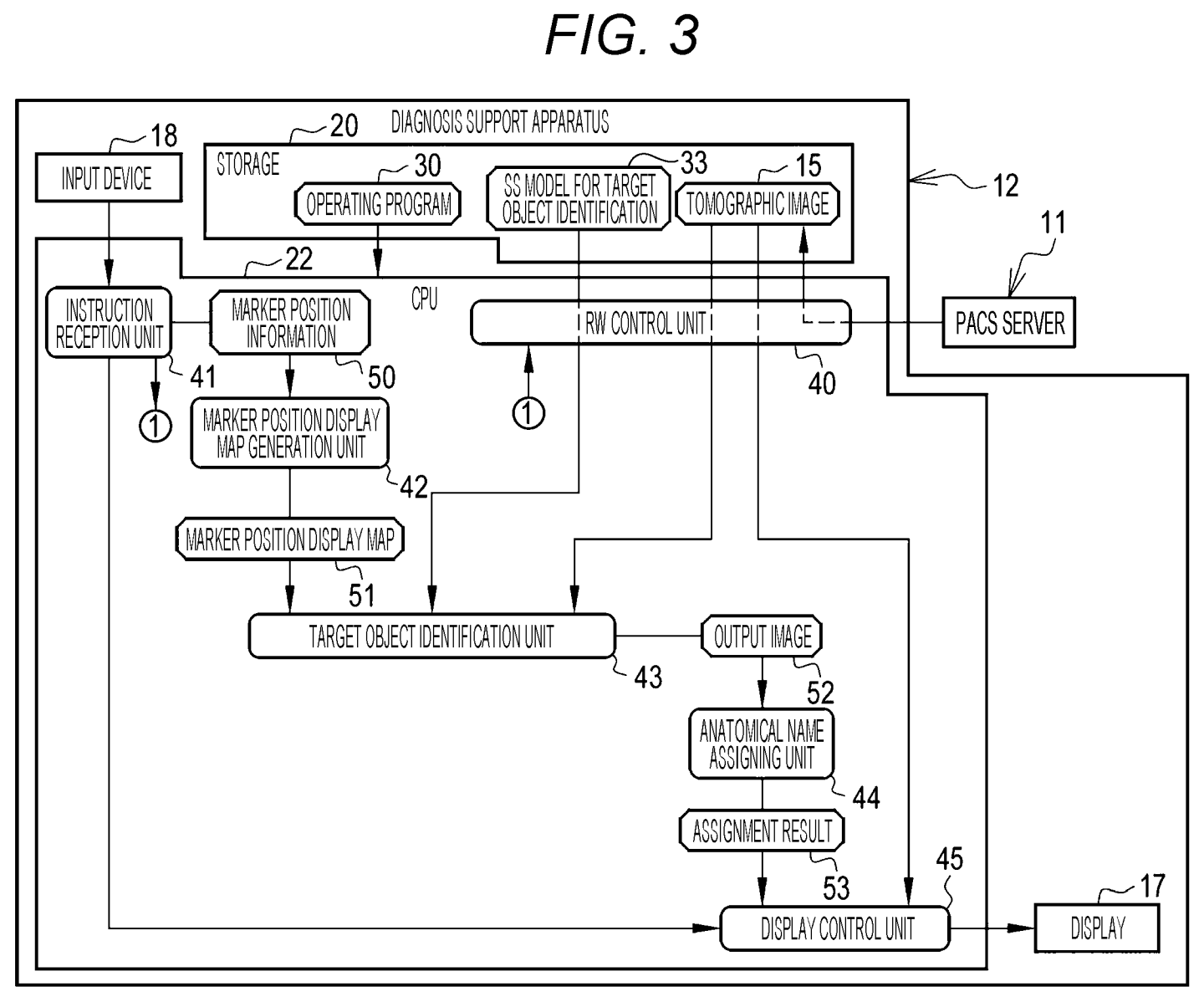

For example, as illustrated in FIG. 3, an operating program 30 is stored in the storage 20 of the diagnosis support apparatus 12. The operating program 30 is an application program that causes the computer constituting the diagnosis support apparatus 12 to function as an "image processing apparatus" according to the technology of the present disclosure. That is, the operating program 30 is an example of a "program for operating an image processing apparatus" according to the technology of the present disclosure. The storage 20 also stores the tomographic image 15 and a semantic segmentation (hereinafter, abbreviated as SS) model 33 for target object identification. The SS model 33 for target object identification is an example of a "semantic segmentation model" according to the technology of the present disclosure. In addition, the storage 20 stores doctor's findings on the vertebrae VB appearing in the tomographic image 15, data of various screens to be displayed on the display 17, and the like.

In a case where the operating program 30 is started, the CPU 22 of the computer constituting the diagnosis support apparatus 12 cooperates with the memory 21 and the like to function as a read/write (hereinafter, abbreviated as RW) control unit 40, an instruction reception unit 41, a marker position display map generation unit 42, a target object identification unit 43, an anatomical name assigning unit 44, and a display control unit 45.

The RW control unit 40 controls storage of various data in the storage 20 and reading of various data from the storage 20. For example, the RW control unit 40 receives the tomographic image 15 from the PACS server 11 and stores the received tomographic image 15 in the storage 20. In FIG. 3, only one tomographic image 15 is stored in the storage 20, but a plurality of tomographic images 15 may be stored in the storage 20.

The RW control unit 40 reads the tomographic image 15 of the patient P designated by the doctor for diagnosis from the storage 20 and outputs the read tomographic image 15 to the target object identification unit 43 and the display control unit 45. The RW control unit 40 reads the tomographic image 15 from the storage 20 to acquire the tomographic image 15. The RW control unit 40 reads the SS model 33 for target object identification from the storage 20 and outputs the read SS model 33 for target object identification to the target object identification unit 43.

The instruction reception unit 41 receives various instructions from the doctor via the input device 18. Examples of the instructions received by the instruction reception unit 41 include an analysis instruction to analyze the tomographic image 15, an input instruction to input markers MK (see FIG. 5) indicating the positions of the vertebrae VB in the tomographic image 15, and a finding storage instruction to store the findings on the vertebrae VB in the storage 20.

In a case where the instruction reception unit 41 has received the analysis instruction, the instruction reception unit 41 outputs, to the display control unit 45, the fact that the instruction reception unit 41 has received the analysis instruction. In a case where the instruction reception unit 41 has received the the instruction to input the markers MK, the instruction reception unit 41 generates marker position information 50 indicating the positions of the markers MK in the tomographic image 15 and outputs the generated marker position information 50 to the marker position display map generation unit 42. Further, in a case where the instruction reception unit 41 has received the the finding storage instruction, the instruction reception unit 41 outputs, to the RW control unit 40, the findings and the fact that the instruction reception unit 41 has received the finding storage instruction.

The marker position display map generation unit 42 generates a marker position display map 51 indicating the positions of the markers MK in the tomographic image 15 on the basis of the marker position information 50 from the instruction reception unit 41. The marker position display map generation unit 42 outputs the marker position display map 51 to the target object identification unit 43.

The target object identification unit 43 identifies each vertebra VB on the basis of the tomographic image 15 and the marker position display map 51. More specifically, the target object identification unit 43 inputs the tomographic image 15 and the marker position display map 51 to the SS model 33 for target object identification, and outputs, from the SS model 33 for target object identification, an output image 52 (see also FIG. 12) in which each vertebra VB is identified. The target object identification unit 43 outputs the output image 52 to the anatomical name assigning unit 44.

The anatomical name assigning unit 44 assigns an anatomical name to each vertebra VB identified in the output image 52. The anatomical name assigning unit 44 outputs an assignment result 53, which is a result of the assignment of the anatomical names to the vertebrae VB, to the display control unit 45.

The display control unit 45 controls display of various screens on the display 17. The various screens include a first screen 60 (see FIG. 4) for giving an instruction to analyze the tomographic image 15 by the marker position display map generation unit 42, the target object identification unit 43, and the anatomical name assigning unit 44, a second screen 70 (see FIG. 5) for giving an instruction to input the markers MK, a third screen 115 (see FIG. 15) for displaying the assignment result 53, and the like.

Figure 4:
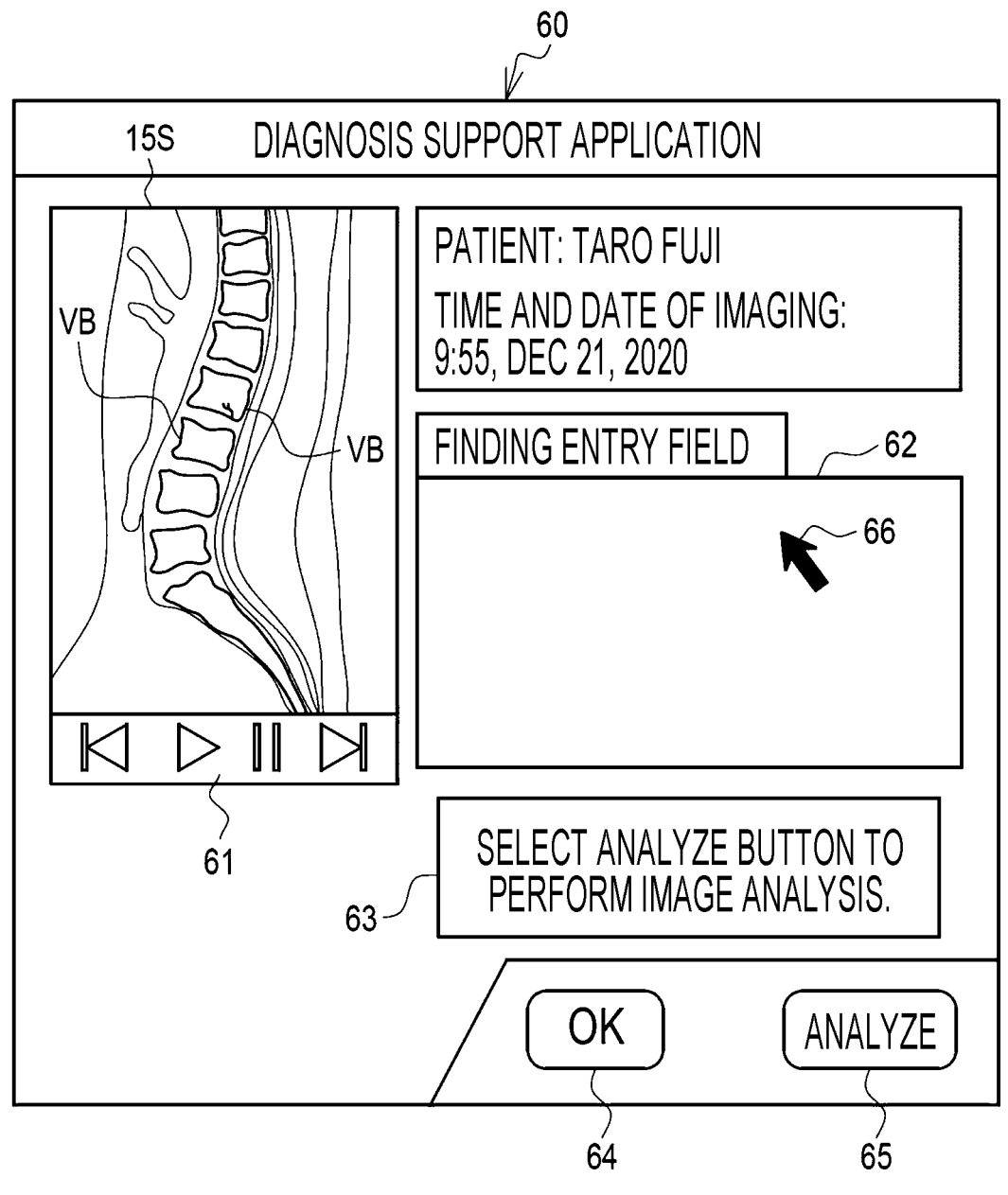
FIG. 4 is a diagram illustrating a first screen.

FIG. 4 illustrates an example of the first screen 60 for giving an instruction to analyze the tomographic image 15. For example, the tomographic image 15S of the sagittal cross section of the patient P for diagnosis of the spine SP is displayed on the first screen 60. A button group 61 for switching the display is provided below the tomographic image 15S. Tomographic images 15 of the axial cross section and the coronal cross section may be displayed instead of or in addition to the tomographic image 15S of the sagittal cross section.

A finding entry field 62, a message 63, an OK button 64, and an analyze button 65 are displayed on the first screen 60. The doctor enters findings on the vertebrae VB in the finding entry field 62. After entering the findings in the finding entry field 62, the doctor places a cursor 66 on the OK button 64 to select the OK button 64. Then, the instruction reception unit 41 receives the finding storage instruction. The RW control unit 40 stores the tomographic image 15 and the findings entered in the finding entry field 62 in association with each other in the storage 20.

The message 63 prompts the user to select the analyze button 65. In a case where the doctor wants to analyze the tomographic image 15 prior to the entry of the findings, the doctor places the cursor 66 on the analyze button 65 to select the analyze button 65. As a result, the instruction reception unit 41 receives the instruction to analyze the tomographic image 15, and outputs, to the display control unit 45, the fact that the instruction reception unit 41 has received the instruction.

Figure 5:
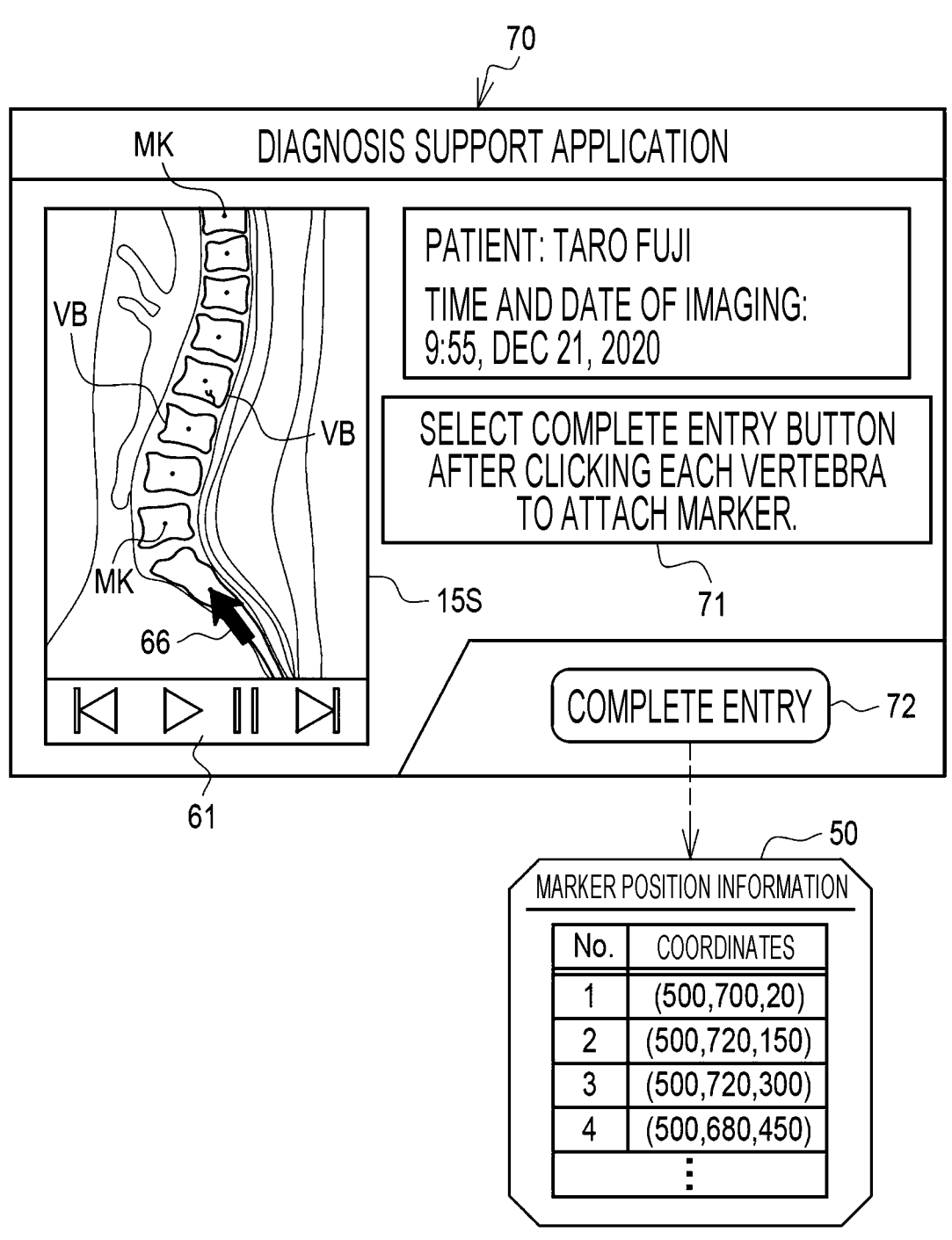
FIG. 5 is a diagram illustrating a second screen.

In a case where the display control unit 45 has received the fact that the instruction to analyze the tomographic image 15 from the instruction reception unit 41, the display control unit 45 causes the screen to transition from the first screen 60 to the second screen 70 illustrated in FIG. 5 as an example.

A message 71 and a complete entry button 72 are displayed on the second screen 70. The message 71 has content for prompting the user to select the complete entry button 72 after the markers MK are attached to the vertebrae VB. The doctor clicks on any point within each vertebra VB, for example, a point considered as the center of each vertebral body with the cursor 66. Accordingly, the markers MK are attached to the vertebrae VB. In this example, each of the markers MK is a point corresponding to a pixel 86 (see FIG. 8) of the tomographic image 15.

After attaching the markers MK to all the vertebrae VB appearing in the tomographic image 15, the doctor places the cursor 66 on the complete entry button 72 to select the complete entry button 72. As a result, the instruction reception unit 41 receives the instruction to input the markers MK. In this case, the marker position information 50 generated by the instruction reception unit 41 is XYZ coordinates of each marker MK. The X-axis is an axis parallel to the left-right direction, the Y-axis is an axis parallel to the front-back direction, and the Z-axis is an axis parallel to the vertical direction. In this example, since the markers MK are attached to the tomographic image 15S of the sagittal cross section, the values of the X coordinates among the XYZ coordinates of the markers MK are the same for each marker MK. The values of the Y coordinates and the Z coordinates are different for each marker MK. In the marker position information 50, numbers (No.) are allocated in ascending order of Z coordinate, and the markers MK are organized.

Figure 6:
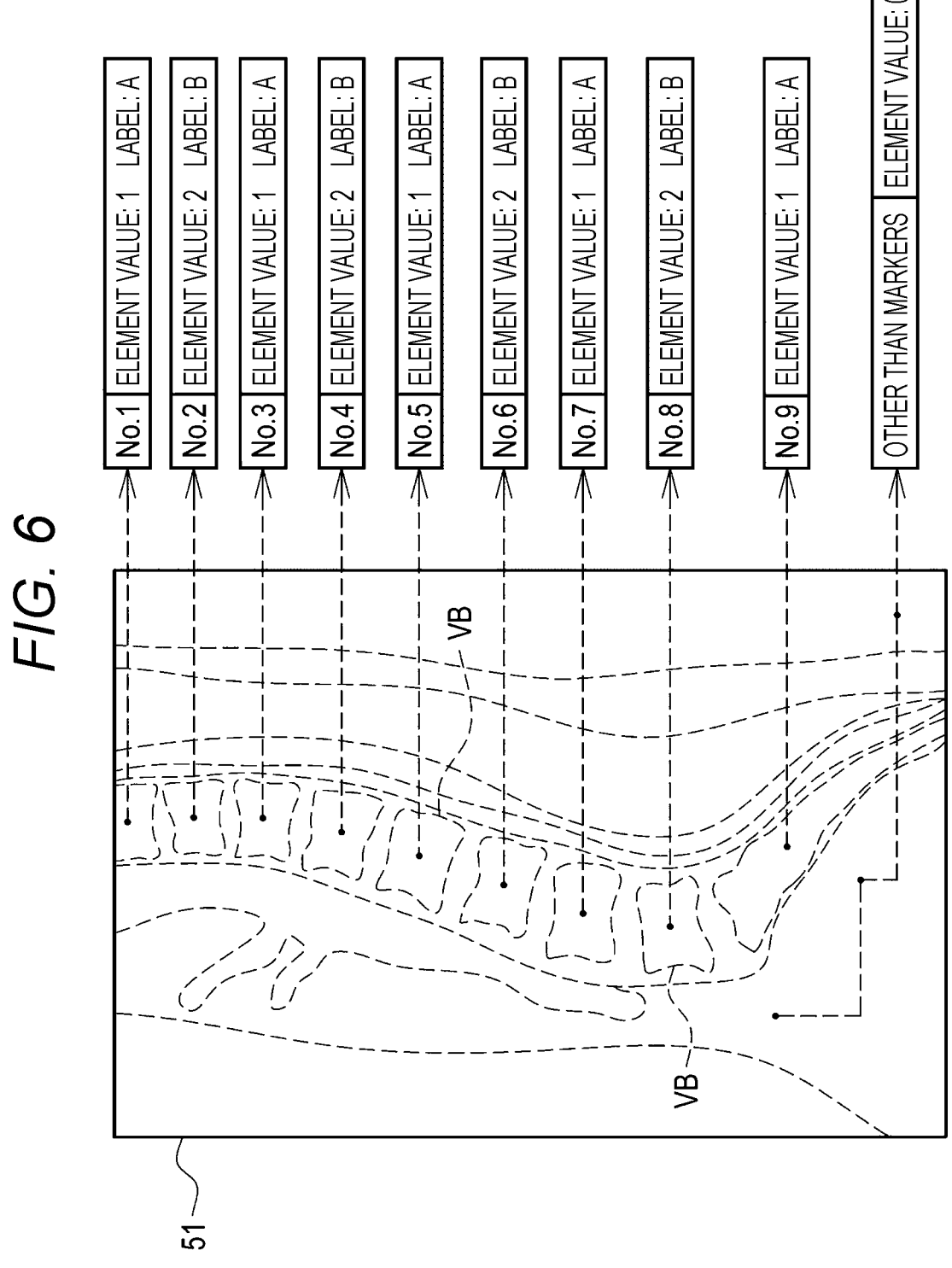
FIG. 6 is a diagram illustrating a marker position display map.

As an example, as illustrated in FIG. 6, the marker position display map 51 is data that has elements 87 (see FIG. 8) in one-to-one correspondence with the pixels 86 of the tomographic image 15, and in which each of the element values of the elements 87 corresponding to the pixels 86 of the markers MK is 1 or 2, and the element values of the elements 87 corresponding to the pixels 86 other than the markers MK are 0. That is, the marker position display map 51 is data in which each of the positions of the markers MK is represented by an element value 1 or 2. In FIG. 6, the vertebrae VB and the like are indicated by broken lines for ease of understanding, but the vertebrae VB and the like do not appear in the actual marker position display map 51.

The marker position display map generation unit 42 attaches a label A to one of two adjacent vertebrae VB such that the element value of the one vertebra VB is 1, and attaches a label B to the other vertebra VB such that the element value of the other vertebra VB is 2. For example, the label A is attached to the No. 1 vertebra VB such that the element value of the No. 1 vertebra VB is 1, and the label B is attached to the No. 2 vertebra VB such that the element value of the No. 2 vertebra VB is 2. In addition, the label A is attached to the No. 7 vertebra VB such that the element value of the No. 7 vertebra VB is 1, and the label B is attached to the No. 8 vertebra VB such that the element value of the No. 8 vertebra VB is 2. The marker position display map generation unit 42 attaches the labels A and B in this way, and as a result, attaches the label A to the Nos. 1, 3, 5, 7, and 9 vertebrae VB, and attaches the label B to the Nos. 2, 4, 6, and 8 vertebrae VB. That is, the labels A and B are alternately attached to the vertebrae VB. Each of the Nos. 1, 3, 5, 7, and 9 vertebrae VB is an example of a "first target object" according to the technology of the present disclosure, and each of the Nos. 2, 4, 6, and 8 vertebrae VB is an example of a "second target object" according to the technology of the present disclosure. Further, the label A is an example of a "first label" according to the technology of the present disclosure, and the label B is an example of a "second label" according to the technology of the present disclosure.

Figure 7:
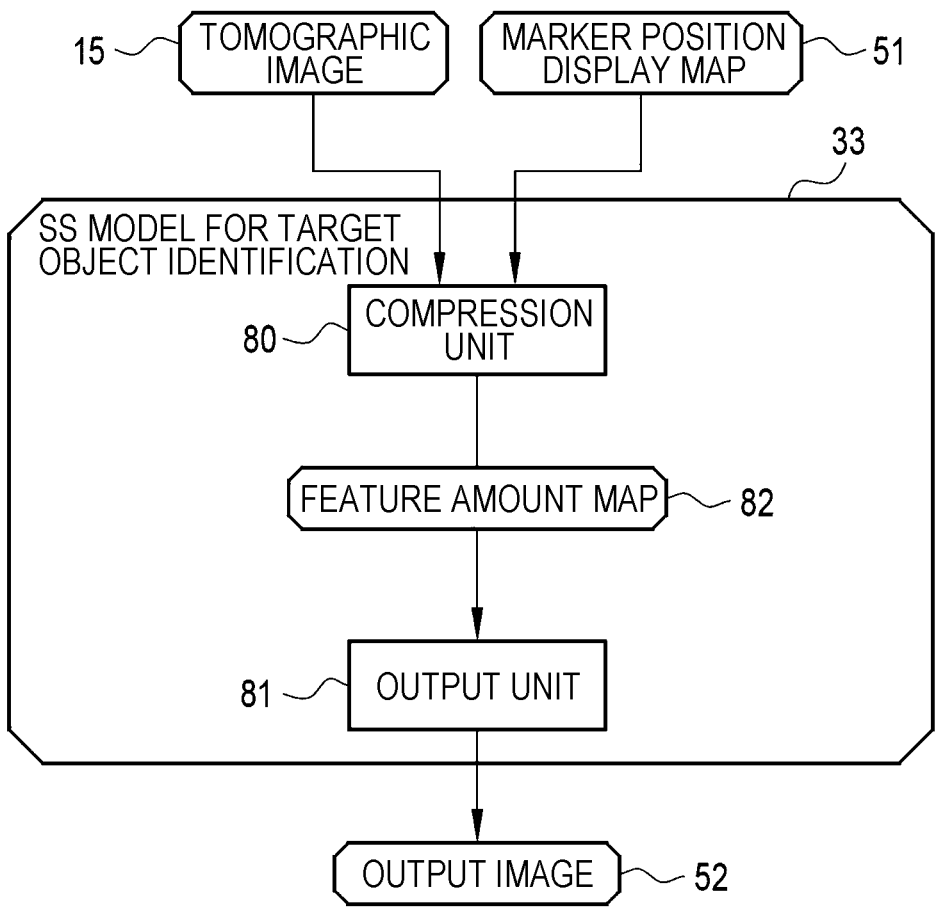
FIG. 7 is a diagram illustrating a semantic segmentation model for target object identification.

As an example, as illustrated in FIG. 7, the SS model 33 for target object identification includes a compression unit 80 and an output unit 81. The tomographic image 15 and the marker position display map 51 are input to the compression unit 80. The tomographic image 15 input to the compression unit 80 is, for example, the tomographic image 15S of the sagittal cross section that is the source of the generation of the marker position display map 51. The compression unit 80 converts the tomographic image 15 and the marker position display map 51 into a feature amount map 82. The compression unit 80 sends the feature amount map 82 to the output unit 81. The output unit 81 outputs the output image 52 on the basis of the feature amount map 82.

Figure 8:
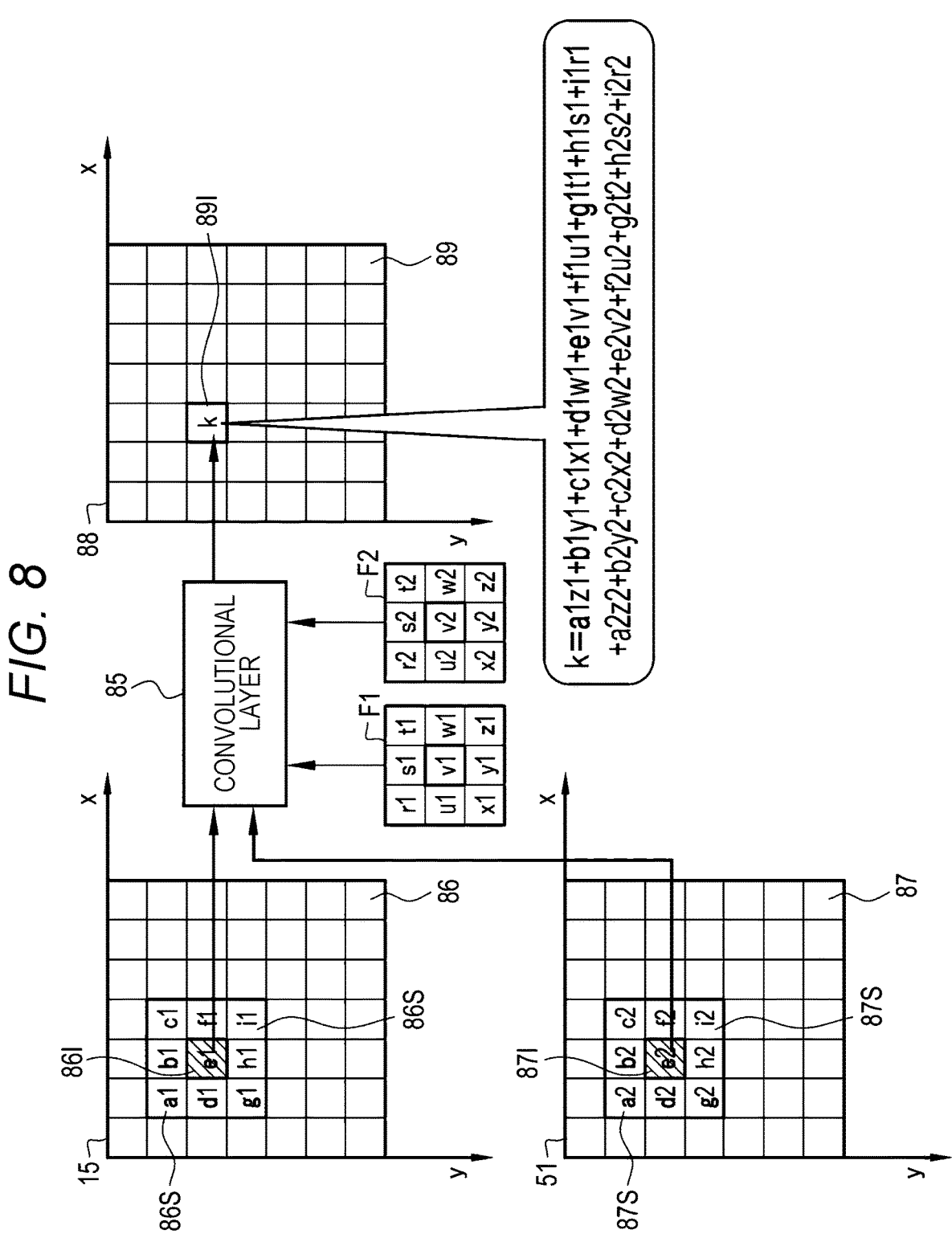
FIG. 8 is an explanatory diagram of convolution processing performed on a tomographic image and the marker position display map.

For example, the compression unit 80 performs a convolution operation as illustrated in FIG. 8 to combine the tomographic image 15 and the marker position display map 51 in a channel direction.

The compression unit 80 has a convolutional layer 85 to which the tomographic image 15 and the marker position display map 51 are input. The convolutional layer 85 applies, for example, a 3×3 filter F1 to the tomographic image 15 having the plurality of pixels 86 arranged two-dimensionally. In addition, the convolutional layer 85 applies, for example, a 3×3 filter F2 to the marker position display map 51 having a plurality of elements 87 two-dimensionally arranged. Then, the convolutional layer 85 convolves a pixel value e1 of one pixel 861 of interest among the pixels 86, pixel values a1, b1, c1, d1, f1, g1, h1, and i1 of eight pixels 86S adjacent to the pixel 861 of interest, an element value e2 of an element 871 of interest, which is one of the elements 87 and corresponds to the pixel 861 of interest, and element values a2, b2, c2, d2, f2, g2, h2, and i2 of eight elements 87S adjacent to the element 871 of interest. The convolutional layer 85 outputs element values of elements 89 of operation data 88 by sequentially performing the convolution operation while shifting the pixel 861 of interest and the element 871 of interest one by one. As a result, the operation data 88 having a plurality of elements 89 arrayed two-dimensionally is obtained. In this manner, the tomographic image 15 and the marker position display map 51 are combined in the channel direction.

The filter F1 has coefficients r1, s1, t1, u1, v1, w1, x1, y1, and z1. Further, the filter F2 has coefficients r2, s2, t2, u2, v2, w2, x2, y2, and z2. In this case, an element value k of an element 891 of the operation data 88 is a result of the convolution operation performed on the pixel 861 of interest and the element 871 of interest and is obtained by calculating, for example, the following Equation (1).

$$k=a1z1+b1y1+c1x1+d1w1+e1v1+f1u1+g1t1+h1s1+ \\ i1r1+a2z2+b2y2+c2x2+d2w2+e2v2+f2u2+g2t2+ \\ h2s2+i2r2 \quad\quad (1)$$

Figure 9:
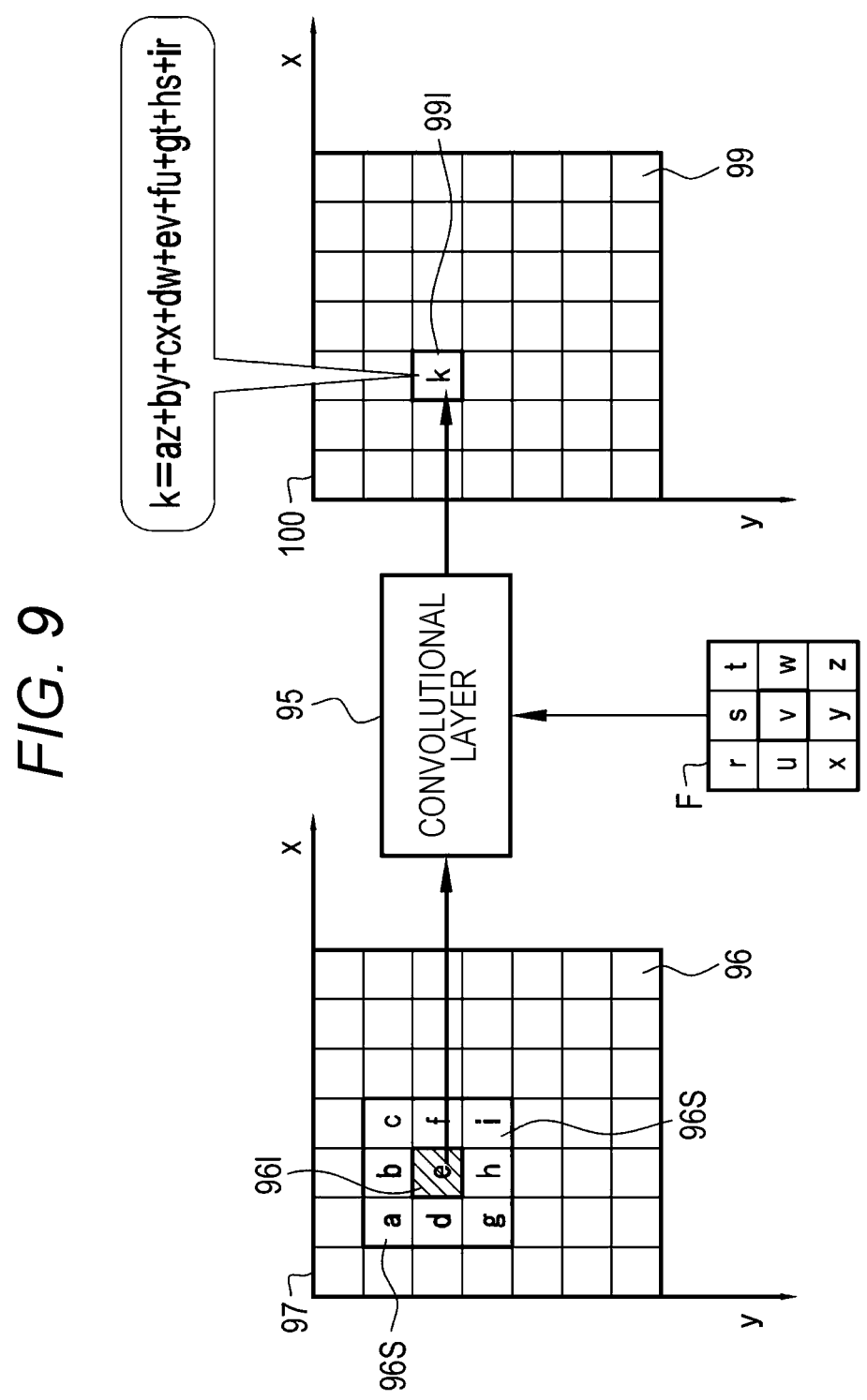
FIG. 9 is an explanatory diagram of convolution processing performed on target data.

As an example, as illustrated in FIG. 9, the compression unit 80 further includes a plurality of convolutional layers 95 in addition to the convolutional layer 85. Each of the convolutional layers 95 applies, for example, a 3×3 filter F to target data 97 having a plurality of elements 96 arranged two-dimensionally. Then, the convolutional layer 95 convolves the element value e of one element 961 of interest among the elements 96 and the element values a, b, c, d, f, g, h, and i of eight elements 96S adjacent to the element 961 of interest. The convolutional layer 95 outputs element values of elements 99 of operation data 100 by sequentially performing the convolution operation on each element 96 of the target data 97 while shifting the element 961 of interest one by one. As a result, the operation data 100 including a plurality of elements 99 arranged two-dimensionally is obtained. The target data 97 input to the convolutional layer 95 is, for example, the operation data 88 illustrated in FIG. 8 or reduction operation data 100S (see FIG. 11) described later.

In a case where the filter F has coefficients r, s, t, u, v, w, x, y, and z, an element value k of an element 991 of the operation data 100 is a result of the convolution operation performed on the element 961 of interest and is obtained by calculating, for example, the following Equation (2).

$$k=az+by+cx+dw+ev+fu+gt+hs+ir \quad\quad (2)$$

Figure 10:
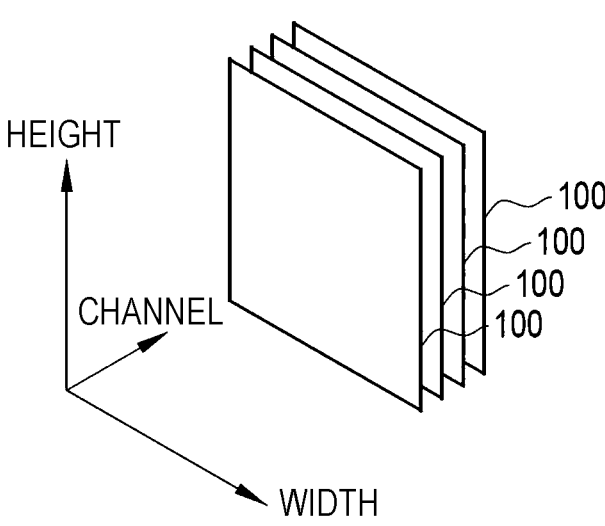
FIG. 10 is a diagram illustrating a configuration of operation data.

One piece of the operation data 100 is output for one filter F. In a case where a plurality of types of filters F are applied to one piece of the target data 97, each piece of the operation data 100 is output for each filter F. That is, for example, as illustrated in FIG. 10, the operation data 100 is generated for the number of filters F applied to the target data 97. Further, the operation data 100 has a width and a height because the operation data 100 has the plurality of elements 99 arranged two-dimensionally. The number of pieces of the operation data 100 is referred to as the number of channels. FIG. 10 illustrates four channels of the operation data 100 output by applying four filters F to one piece of the target data 97.

Figure 11:
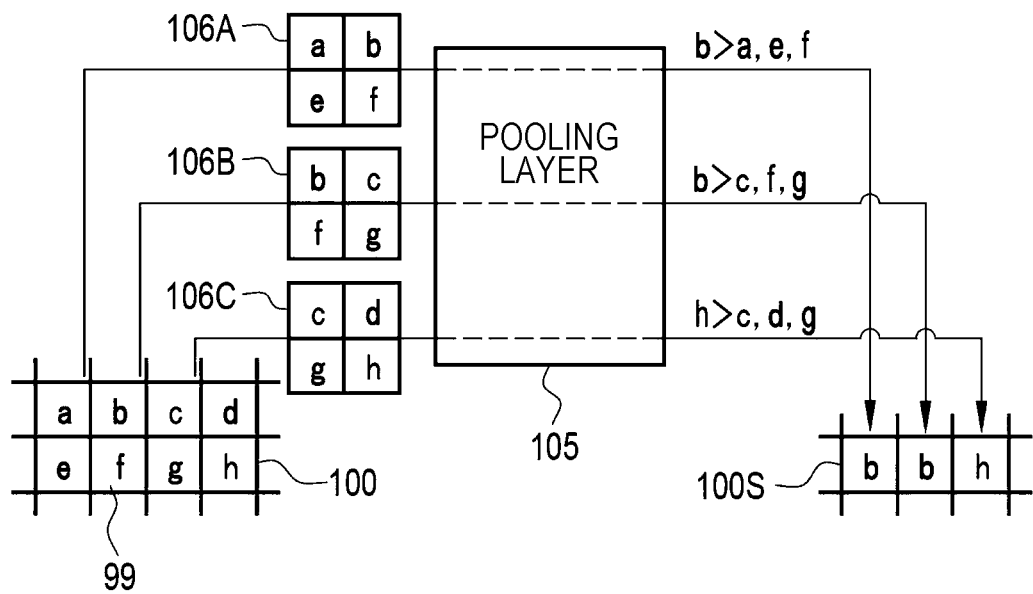
FIG. 11 is an explanatory diagram of pooling processing.

As an example, as illustrated in FIG. 11, the compression unit 80 includes a pooling layer 105 in addition to the convolutional layers 85 and 95. The pooling layer 105 obtains a local statistic value of the element values of the elements 99 of the operation data 100, and generates reduction operation data 100S having the obtained statistic value as an element value. In this case, the pooling layer 105 performs maximum value pooling processing for obtaining the maximum value among element values in a block 106 of 2×2 elements as the local statistic value. In a case where the processing is performed while shifting the elements in the block 106 one by one in the width direction and the height direction, the size of the reduction operation data 100S is reduced to ½ of the original operation data 100. FIG. 11 illustrates a case where b is the maximum value among element values a, b, e, and f in a block 106A, b is the maximum value among element values b, c, f, and g in a block 106B, and h is the maximum value among element values c, d, g, and h in a block 106C. Average value pooling processing for obtaining average values as local statistic values instead of the maximum values may be performed.

The compression unit 80 outputs final operation data 100 by repeating the convolution processing by the convolutional layers 85 and 95 and the pooling processing by the pooling layer 105 a plurality of times. The final operation data 100 is the feature amount map 82. Although not illustrated, the compression unit 80 also performs skip layer processing or the like for sending the operation data 100 to the output unit 81.

The output unit 81 performs upsampling processing for enlarging the size of the feature amount map 82 to obtain an enlarged feature amount map. The output unit 81 also performs convolution processing at the same time in the upsampling processing. In addition, the output unit 81 performs merge processing for combining the enlarged feature amount map and the operation data 100 received from the compression unit 80 in the skip layer processing. The output unit 81 further performs convolution processing after the merge processing. Through such various types of processing, the output unit 81 outputs the output image 52 from the feature amount map 82.

As described above, the SS model 33 for target object identification is constructed by a CNN. Examples of the CNN include U-Net and residual network (ResNet) (Residual Network).

Figure 12:
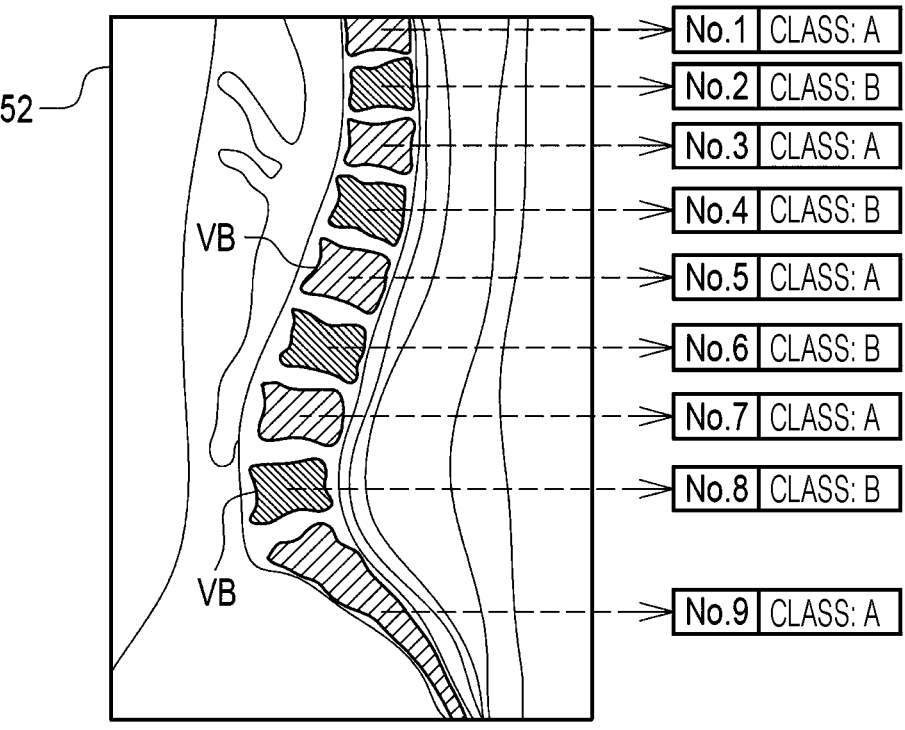
FIG. 12 is a diagram illustrating an output image.

As an example, as illustrated in FIG. 12, the output image 52 is an image in which each vertebra VB is labeled with a class. Specifically, the output image 52 is an image in which the Nos. 1, 3, 5, 7, and 9 vertebrae VB are identified as a class A corresponding to the label A, and the Nos. 2, 4, 6, and 8 vertebrae VB are identified as a class B corresponding to the label B. The class A is an example of a "first class" according to the technology of the present disclosure, and the class B is an example of a "second class" according to the technology of the present disclosure.

Figure 13:
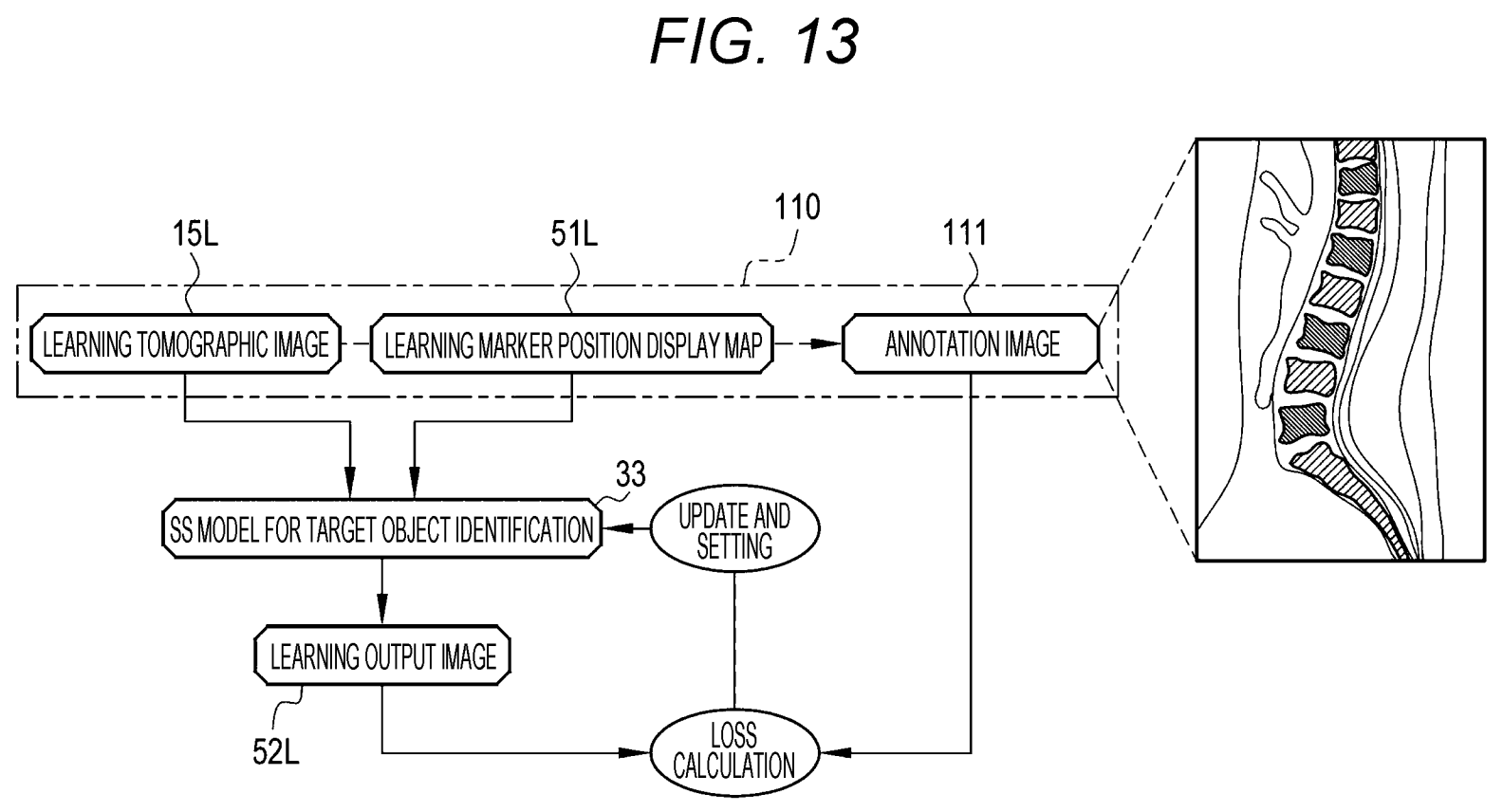

As an example, as illustrated in FIG. 13, the SS model 33 for target object identification is trained by being given learning data (also referred to as teacher data) 110 in the learning phase. The learning data 110 is a set of a learning tomographic image 15L, a learning marker position display map 51L corresponding to the learning tomographic image 15L, and an annotation image 111 corresponding to the learning tomographic image 15L and the learning marker position display map 51L. The learning marker position display map 51L is obtained by attaching the markers MK to the vertebrae VB appearing in the learning tomographic image 15L and alternately attaching labels A and B to the vertebrae VB appearing in the learning tomographic image 15L. The annotation image 111 is an image obtained by labeling the vertebrae VB appearing in the learning tomographic image 15L with the classes corresponding to the labels attached in the learning marker position display map 51L.

In the learning phase, the learning tomographic image 15L and the learning marker position display map 51L are input to the SS model 33 for target object identification. The SS model 33 for target object identification outputs a learning output image 52L for the learning tomographic image 15L and the learning marker position display map 51L. A loss of the SS model 33 for target object identification is calculated on the basis of the learning output image 52L and the annotation image 111. Then, the various coefficients (coefficients of the filter F and the like) of the SS model 33 for target object identification are updated and set according to the result of the loss calculation, and the SS model 33 for target object identification is updated according to the update and setting of the coefficients.

In the learning phase of the SS model 33 for target object identification, the series of processes of inputting the learning tomographic image 15L and the learning marker position display map 51L to the SS model 33 for target object identification and outputting the learning output image 52L from the SS model 33 for target object identification, the loss calculation, the update and setting, and the update of the SS model 33 for target object identification are repeatedly performed while the learning data 110 is exchanged. The repetition of the series of processes is ended in a case where the accuracy of prediction of the learning output image 52L for the annotation image 111 reaches a predetermined set level. The SS model 33 for target object identification of which the prediction accuracy reaches the set level is stored in the storage 20 and is used in the target object identification unit 43. Regardless of the accuracy of the prediction of the learning output image 52 L for the annotation image 111, the learning may be ended when the series of processes is repeated a set number of times.

Figure 14:
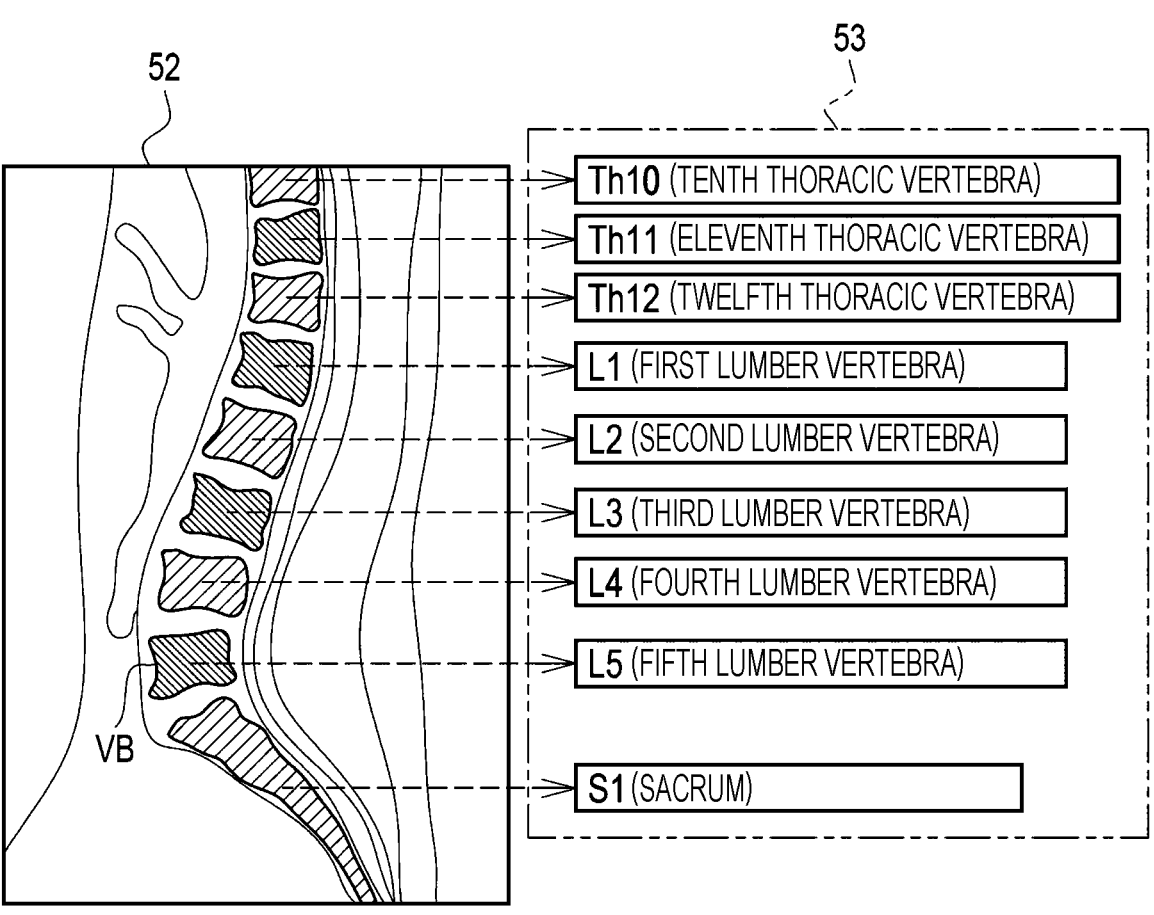
FIG. 14 is a diagram illustrating a labeling result.

As an example, as illustrated in FIG. 14, the assignment result 53 is anatomical names of the vertebrae VB, such as a Th10 (tenth thoracic vertebra), an L1 (first lumbar vertebra), and an Si (sacrum).

Figure 15:
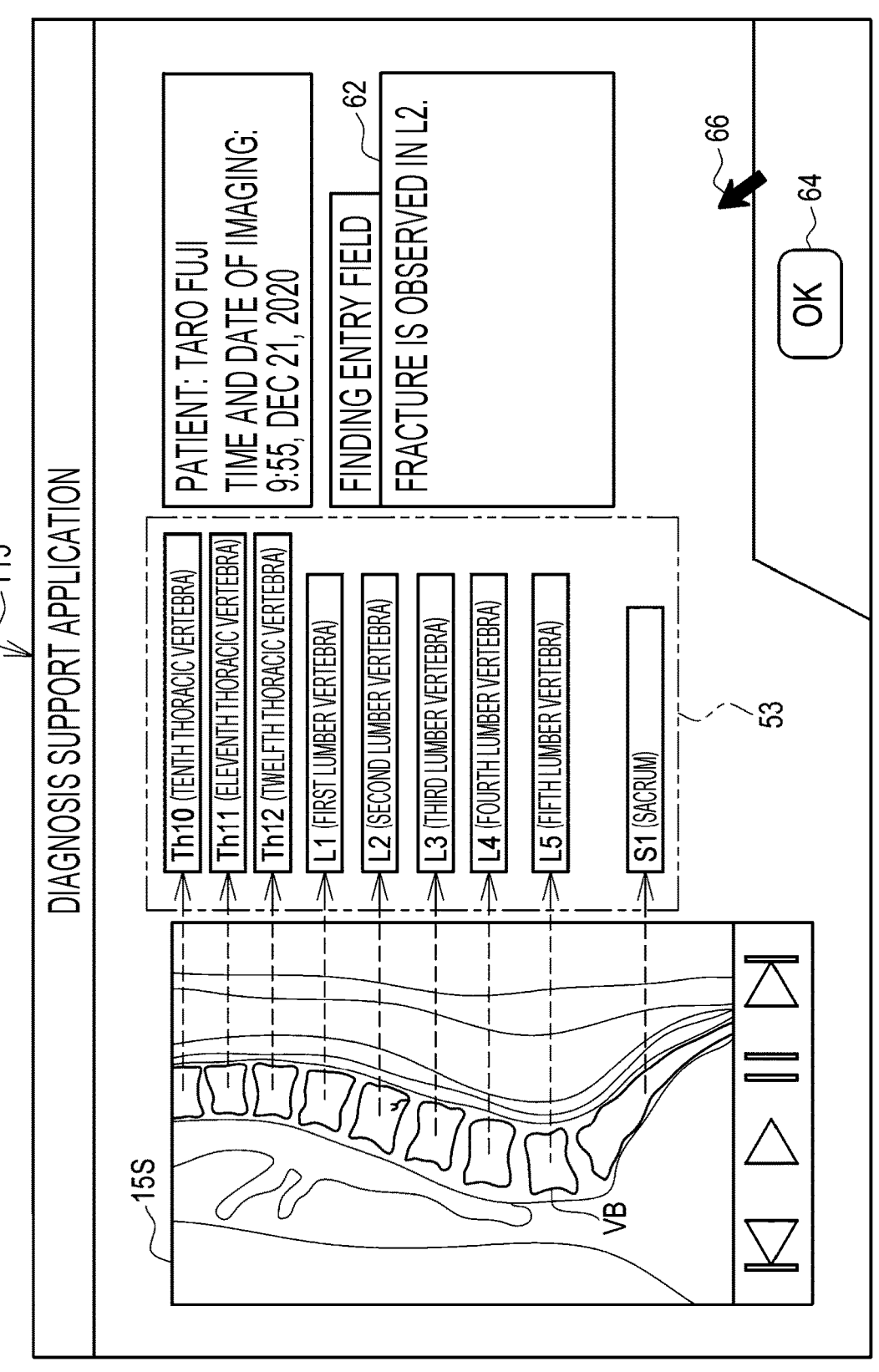
FIG. 15 is a diagram illustrating a third screen.

FIG. 15 illustrates an example of a third screen 115 displaying the assignment result 53. The display control unit 45 causes the screen to transition from the second screen 70 illustrated in FIG. 5 to the third screen 115. The assignment result 53 is displayed next to the tomographic image 15 on the third screen 115. Similar to the first screen 60 illustrated in FIG. 4, the finding entry field 62 and the OK button 64 are displayed on the third screen 115. The doctor enters the findings in the finding entry field 62 with reference to the assignment result 53 and then places the cursor 66 on the OK button 64 to select the OK button 64. As a result, the instruction reception unit 41 receives the finding storage instruction as in a case of FIG. 4. The RW control unit 40 stores the tomographic image 15 and the findings entered in the finding entry field 62 in association with each other in the storage 20.

Figure 16:
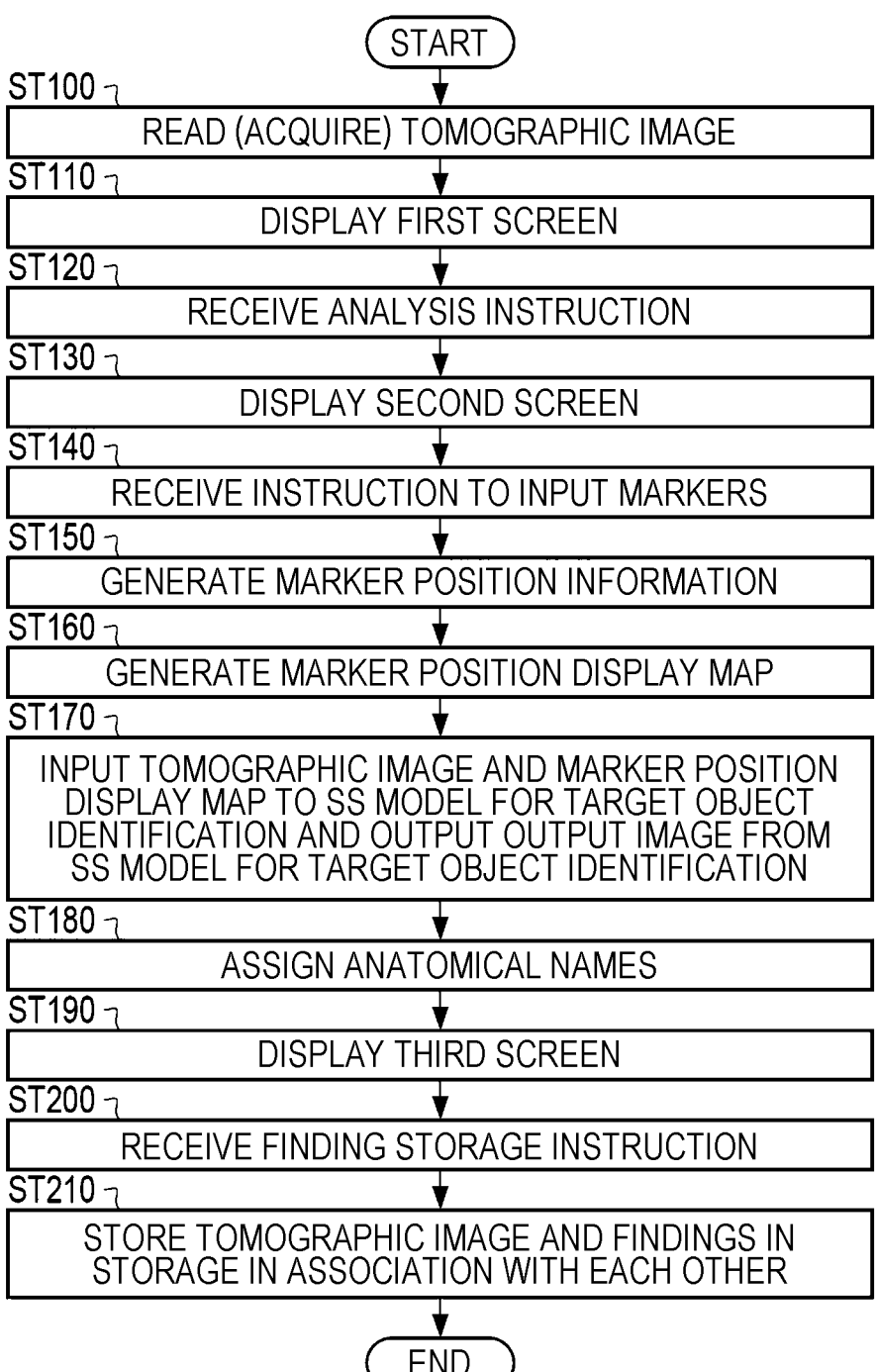
FIG. 16 is a flowchart illustrating a processing procedure of the diagnosis support apparatus.

Next, the operation of the above-described configuration will be described referring to a flowchart of FIG. 16. First, when the operating program 30 is started in the diagnosis support apparatus 12, as illustrated in FIG. 3, the CPU 22 of the diagnosis support apparatus 12 functions as the RW control unit 40, the instruction reception unit 41, the marker position display map generation unit 42, the target object identification unit 43, the anatomical name assigning unit 44, and the display control unit 45.

The RW control unit 40 reads the tomographic image 15 of the patient P for diagnosing the spine SP from the storage 20 (step ST100). Accordingly, the tomographic image 15 is acquired. The tomographic image 15 is output from the RW control unit 40 to the display control unit 45. Then, the first screen 60 illustrated in FIG. 4 is displayed on the display 17 under the control of the display control unit 45 (step ST110).

In a case where the analyze button 65 is selected by the doctor on the first screen 60, an instruction to analyze the tomographic image 15 is received by the instruction reception unit 41 (step ST120). Under the control of the display control unit 45, the first screen 60 is transitioned to the second screen 70 illustrated in FIG. 5 (step ST130).

In the second screen 70, after the markers MK are attached to the vertebrae VB by the doctor, the complete entry button 72 is selected. As a result, the instruction to input the markers MK is received by the instruction reception unit 41 (step ST140). The instruction reception unit 41 generates the marker position information 50 indicating the positions of the markers MK (step ST150). The marker position information 50 is output from the instruction reception unit 41 to the marker position display map generation unit 42.

The marker position display map generation unit 42 generates the marker position display map 51 illustrated in FIG. 6 on the basis of the marker position information 50 (step ST160). The marker position display map 51 is output from the marker position display map generation unit 42 to the target object identification unit 43.

The tomographic image 15 and the SS model 33 for target object identification are input to the target object identification unit 43 from the RW control unit 40. In the target object identification unit 43, as illustrated in FIG. 7, the tomographic image 15 and the marker position display map 51 are input to the SS model 33 for target object identification. In this case, as illustrated in FIG. 8, the tomographic image 15 and the marker position display map 51 are combined in the channel direction. Then, the output image 52 is output from the SS model 33 for target object identification (step ST170). The output image 52 is output from the target object identification unit 43 to the anatomical name assigning unit 44.

The anatomical name assigning unit 44 assigns an anatomical name to each of the vertebrae VB identified in the output image 52 as illustrated in FIG. 14 (step ST180). The assignment result 53 is output from the anatomical name assigning unit 44 to the display control unit 45.

Under the control of the display control unit 45, the third screen 115 illustrated in FIG. 15 is displayed on the display 17 (step ST190). The doctor enters the findings in the finding entry field 62 with reference to the assignment result 53 and then places the cursor 66 on the OK button 64 to select the OK button 64. As a result, the finding storage instruction is received by the instruction reception unit 41 (step ST200).

Then, under the control of the RW control unit 40, the tomographic image 15 and the findings input to the finding entry field 62 are stored in the storage 20 in association with each other (step ST210).

As described above, the CPU 22 of the diagnosis support apparatus 12 includes the RW control unit 40, the instruction reception unit 41, the marker position display map generation unit 42, and the target object identification unit 43. The RW control unit 40 reads and acquires, from the storage 20, the tomographic image 15 in which the vertebrae VB that are a plurality of contiguous target objects of the same type appear. The instruction reception unit 41 receives inputs of the markers MK indicating the positions of the vertebrae VB in the tomographic image 15. The marker position display map generation unit 42 generates the marker position display map 51 indicating the positions of the markers MK in the tomographic image 15. The target object identification unit 43 inputs the tomographic image 15 and the marker position display map 51 to the SS model 33 for target object identification, and outputs, from the SS model 33 for target object identification, the output image 52 in which each vertebra VB is identified. Therefore, it is possible to increase the accuracy of the identification of the vertebrae VB due to the clue of the markers MK, as compared with a case where the vertebrae VB are identified without any clue.

The marker position display map generation unit 42 generates the marker position display map 51 of the markers MK corresponding to all of the contiguous vertebrae VB. In this case, the marker position display map generation unit 42 attaches the label A to one of every two adjacent vertebrae VB among the contiguous vertebrae VB and attaches the label B to the other of every two adjacent vertebrae VB among the contiguous vertebrae VB. The target object identification unit 43 outputs, from the SS model 33 for target object identification, the output image 52 in which the one of every two adjacent vertebrae VB is identified as the class A corresponding to the label A and the other of every two adjacent vertebrae VB is identified as the class B corresponding to the label B. Therefore, all the vertebrae VB can be identified at once, and the processing time can be shortened.

The target object identification unit 43 combines the tomographic image 15 and the marker position display map 51 in the channel direction in the SS model 33 for target object identification. The processing time can be shortened as compared with a case where the tomographic image 15 and the marker position display map 51 are input to different compression units.

In the learning phase, the learning tomographic image 15L and the learning marker position display map 51L are input to the SS model 33 for target object identification, and the SS model 33 for target object identification outputs the learning output image 52L according to the learning tomographic image 15L and the learning marker position display map 51L. Then, the SS model 33 for target object identification is trained on the basis of the comparison between the learning output image 52L and the annotation image 111 which is generated on the basis of the learning tomographic image 15L and in which the vertebrae VB to which the markers MK are attached are annotated. Therefore, it is possible to obtain the SS model 33 for target object identification that outputs the corresponding output image 52 in response to the input of the tomographic image 15 and the marker position display map 51.

In the medical field, there is a very high demand for performing accurate diagnosis by identifying a body structure with high accuracy. For this reason, it can be said that this example in which the tomographic image 15 which is a medical image obtained by imaging the inside of the body of the patient P is used as an analysis target image and the vertebrae VB which are a structure of the body are used as target objects is a form matching the request.

In addition, the vertebrae VB constituting the spine SP are known as target objects which are particularly difficult to be identified, and various identification methods have been proposed in the related art, and it is an urgent problem to increase the accuracy of the identification. Therefore, it can be said that this example in which the tomographic image 15 obtained by imaging the spine SP of the patient P is used as a medical image and the vertebrae VB constituting the spine SP are used as a structure is a form matching the urgent problem of increasing the accuracy of the identification of the vertebrae VB.

The tomographic image 15 input to the compression unit 80 is not limited to the tomographic image 15S of the sagittal cross section that is the source of the generation of the marker position display map 51. In addition to the tomographic image 15S of the sagittal cross section that is the source of the generation of the marker position display map 51, tomographic images 15S of several sagittal cross sections before and after the tomographic image 15S of the sagittal cross section that is the source of the generation of the marker position display map 51 may be input to the compression unit 80. Alternatively, results of the identification of the vertebrae VB from a tomographic image 15S of one sagittal cross section may be used for tomographic images 15S of several sagittal cross sections before and after the tomographic image 15S of the sagittal cross section.

Each of the markers MK is not limited to a point corresponding to one pixel 86 of the tomographic image 15. Each of the markers MK may be a circular region including several to several tens of pixels 86 centered on a point clicked with the cursor 66. Alternatively, an amorphous region constituted by a plurality of pixels 86 in which the inside of each of the vertebrae VB is roughly filled by the doctor may be used as each of the markers MK. In this case, the marker position display map 51 is data in which each of the element values of the elements 87 corresponding to the plurality of pixels 86 in regions filled by the doctor is set to, for example, 1 or 2, and the element values of the elements 87 corresponding to the pixels 86 other than the regions filled by the doctor are set to 0.

The position where each of the markers MK is attached is not limited to the point that is considered to be the center of the vertebral body of each of the vertebrae VB. The position may be considered as the tip of the spinous process of the vertebral arch. Alternatively, the position may be a point that is considered to be the center of the vertebral foramen through which the spinal cord extends.

In the above example, the element value of the label A is set to 1 and the element value of the label B is set to 2, but the element values are not limited thereto. The element values of the labels A and B need only be different from each other. For example, the element value of the label A may be 1, and the element value of the label B may be −1.

Figure 17:
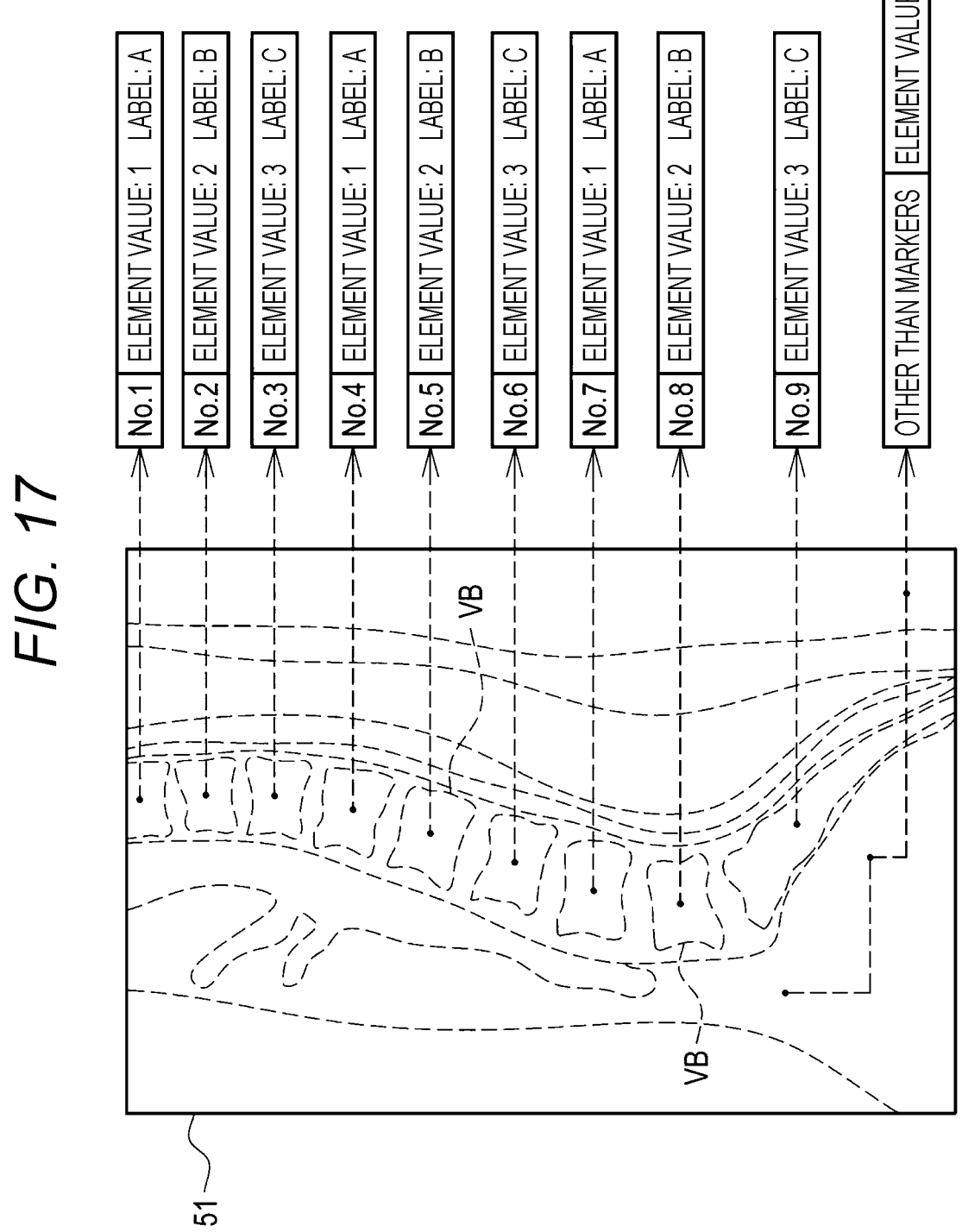
FIG. 17 is a diagram illustrating another example of the marker position display map.
Figure 18:
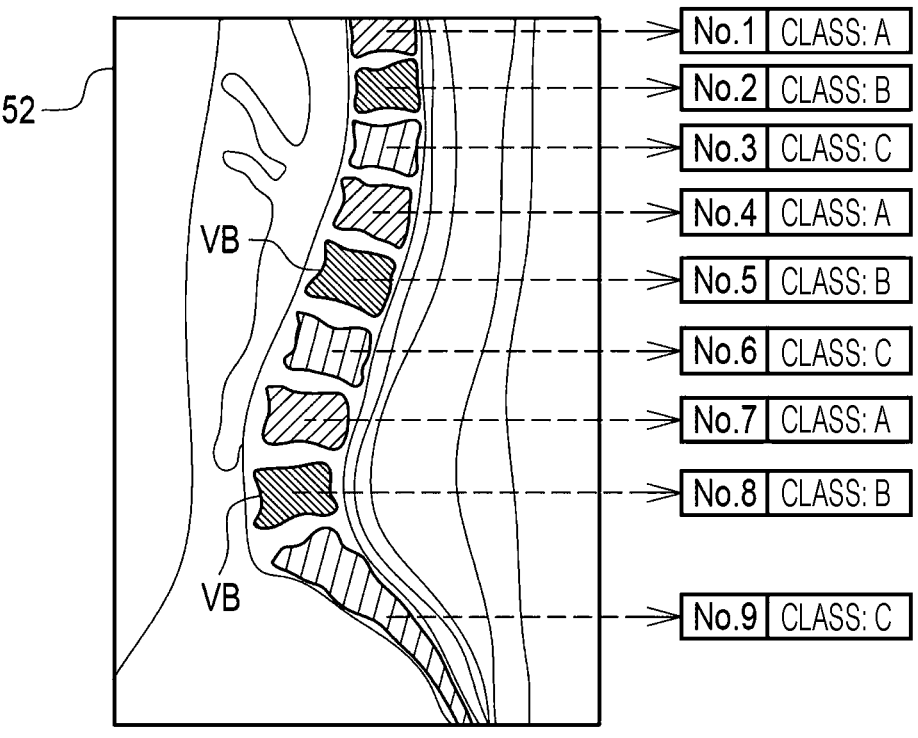
FIG. 18 is a diagram illustrating an output image output on the basis of the marker position display map illustrated in FIG. 17.

The types of labels are not limited to two types of labels A and B. Three or more types of labels may be attached. For example, as illustrated in FIG. 17, the label A may be attached to the Nos. 1, 4, and 7 vertebrae VB such that the element values of the Nos. 1, 4, and 7 vertebrae VB are 1, the label B may be attached to the Nos. 2, 5, and 8 vertebrae VB such that the element values of the Nos. 2, 5, and 8 vertebrae VB are 2, and a label C may be attached to the Nos. 3, 6, and 9 vertebrae VB such that the element values of the Nos. 3, 6, and 9 vertebrae VB are 3. In this case, as illustrated in FIG. 18, the output image 52 is an image in which the Nos. 1, 4, and 7 vertebrae VB are identified as the class A corresponding to the label A, the Nos. 2, 5, and 8 vertebrae VB are identified as the class B corresponding to the label B, and the Nos. 3, 6, and 9 vertebrae VB are identified as a class C corresponding to the label C.

In the above example, a mode in which the vertebrae VB are identified in order to assign the anatomical names of the vertebrae VB has been exemplified, but the present disclosure is not limited thereto. For example, the vertebrae VB may be identified as preprocessing of computer-aided diagnosis (CAD) for extracting lesion candidates, such as a fracture and metastasis of cancer to bone tissue.

Second Embodiment

In the first embodiment, the marker position display map 51 of the markers MK corresponding to all of the plurality of contiguous vertebrae VB is generated, but the present disclosure is not limited thereto. A second embodiment illustrated in FIGS. 19 to 21 may be adopted.

Figure 19:
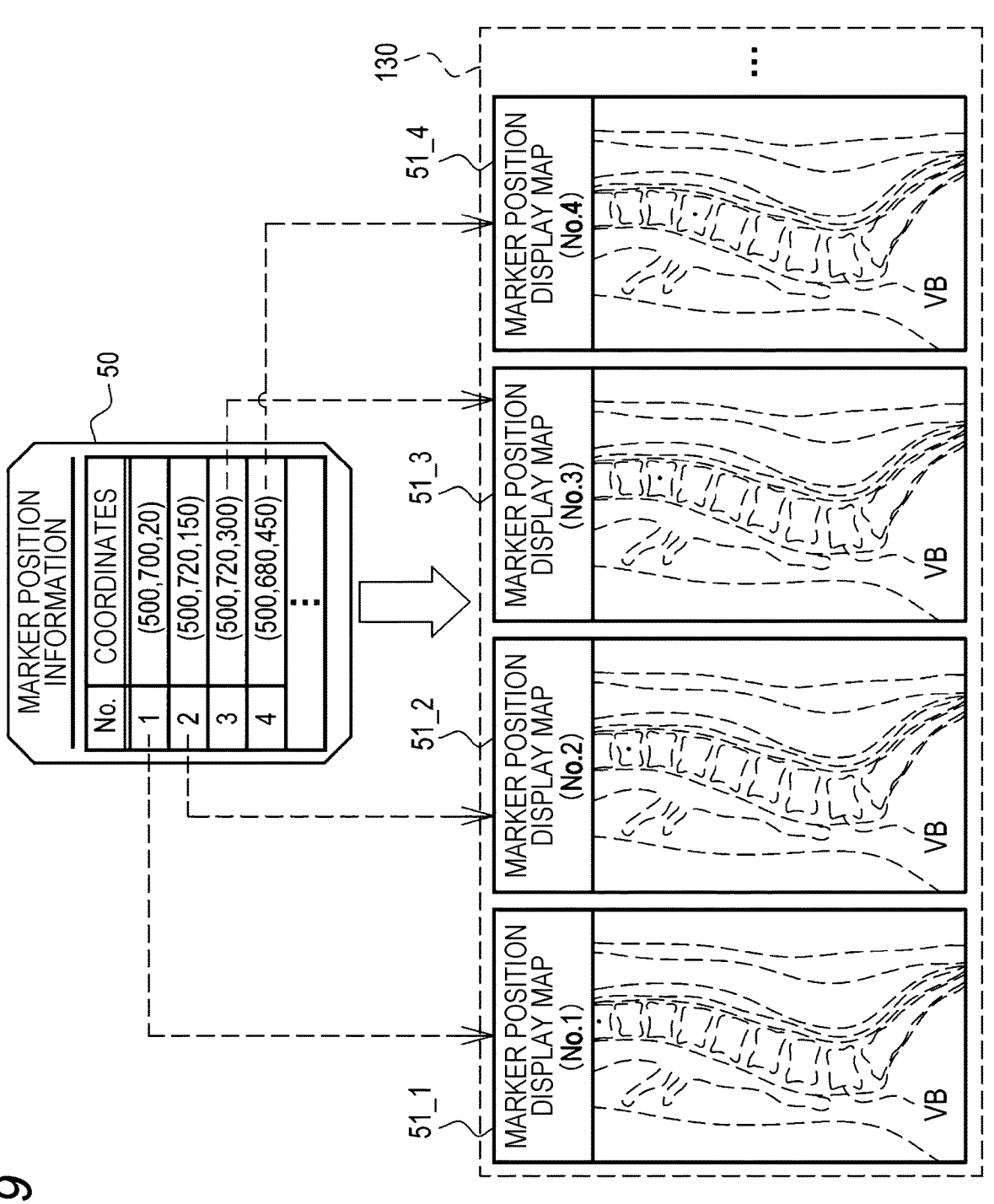
FIG. 19 is a diagram illustrating a state in which a marker position display map of a marker corresponding to one vertebra among a plurality of contiguous vertebrae is generated.

As an example, as illustrated in FIG. 19, the marker position display map generation unit 42 generates a marker position display map group 130 based on the marker position information 50. The marker position display map group 130 includes a marker position display map 51_1 indicating the position of the marker MK attached to the No. 1 vertebra VB, a marker position display map 51_2 indicating the position of the marker MK attached to the No. 2 vertebra VB, a marker position display map 51_3 indicating the position of the marker MK attached to the No. 3 vertebra VB, a marker position display map 51_4 indicating the position of the marker MK attached to the No. 4 vertebra VB, . . . . That is, in this embodiment, the marker position display map generation unit 42 generates a marker position display map 51 of a marker MK corresponding to one vertebra VB among the plurality of contiguous vertebrae VB.

Figure 20:
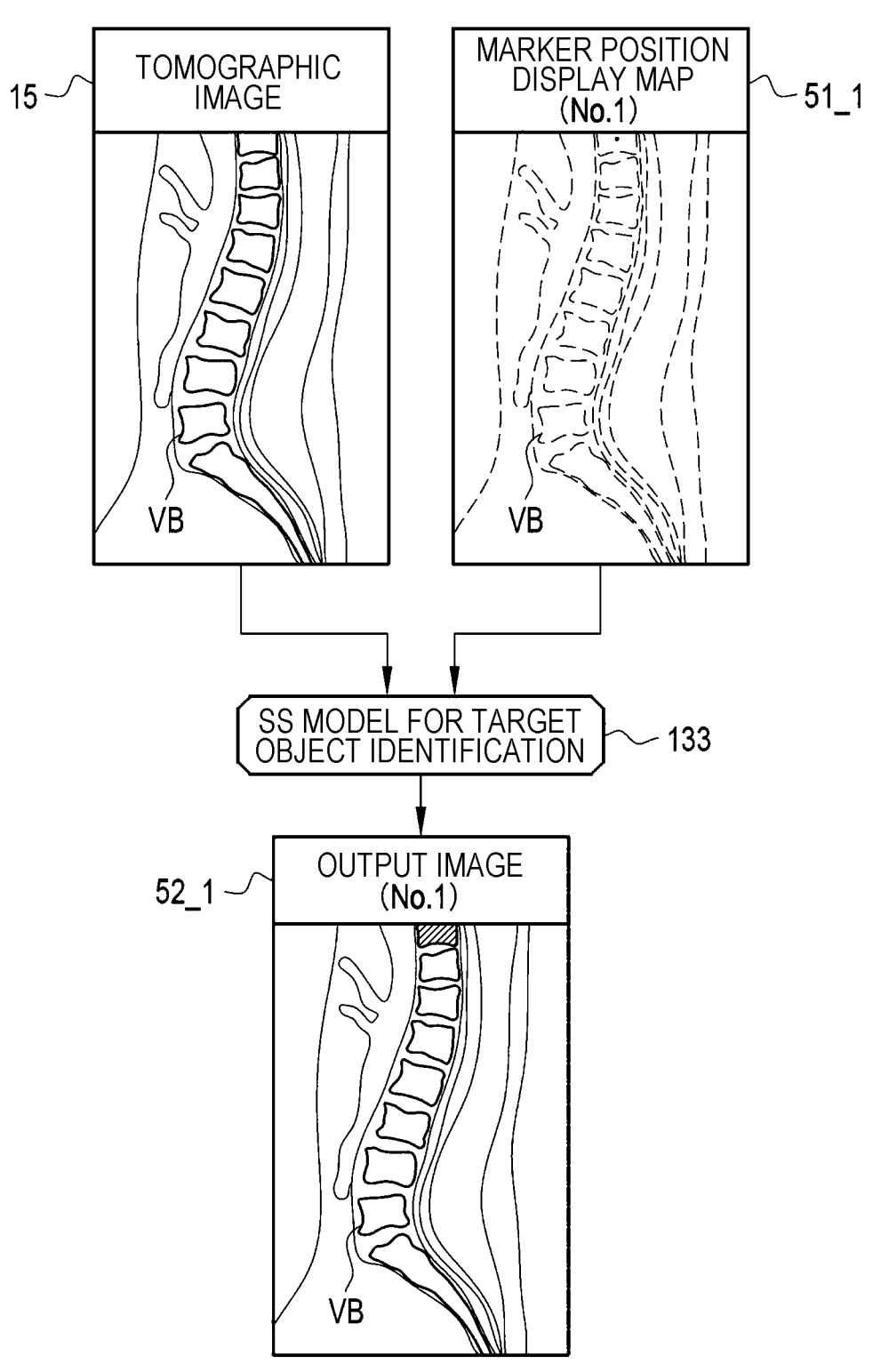
FIG. 20 is a diagram illustrating a state in which a tomographic image and a marker position display map of a marker corresponding to one vertebra are input to a semantic segmentation model for target object identification and an output image in which one vertebra is identified is output from the semantic segmentation model for target object identification.

As an example, as illustrated in FIG. 20, the tomographic image 15 and one of a plurality of marker position display maps 51 constituting the marker position display map group 130 are input to an SS model 133 for target object identification according to the present embodiment. In addition, the SS model 133 for target object identification outputs an output image 52 in which one vertebra VB to which the marker MK whose position is represented in the marker position display map 51 is attached is identified. FIG. 20 illustrates a state in which the marker position display map 51_1 indicating the position of the marker MK attached to the No. 1 vertebra VB is input to the SS model 133 for target object identification together with the tomographic image 15, and an output image 52_1 in which the No. 1 vertebra VB is identified is output from the SS model 133 for target object identification.

In a learning phase, a learning tomographic image 15L and a learning marker position display map 51L of a marker MK corresponding to one vertebra VB are input to the SS model 133 for target object identification. Then, the loss of the SS model 133 for target object identification is calculated on the basis of a learning output image 52L output from the SS model 133 for target object identification and an annotation image in which the one vertebra VB to which the marker MK is attached is annotated.

Figure 21:
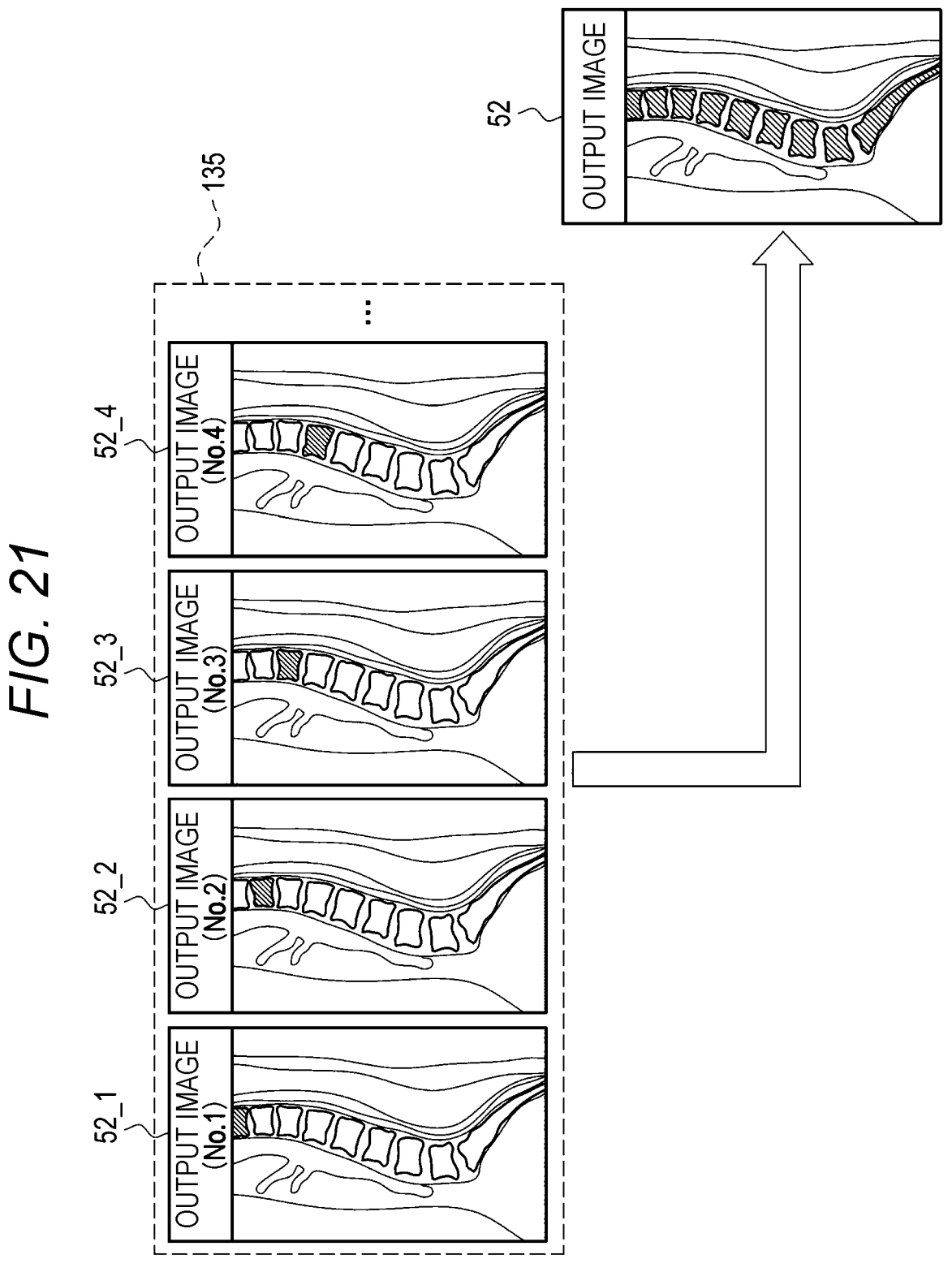
FIG. 21 is a diagram illustrating a state in which an output image in which each vertebra is identified is generated from an output image in which one vertebra is identified.

By repeating the processing illustrated in FIG. 20 on each marker position display map 51, an output image group 135 illustrated in FIG. 21 is obtained as an example. The output image group 135 includes an output image 52_1 in which the No. 1 vertebra VB is identified, an output image 52_2 in which the No. 2 vertebra VB is identified, an output image 523 in which the No. 3 vertebra VB is identified, and an output image 52_4 in which the No. 4 vertebra VB is identified, . . . . The target object identification unit 43 generates, from the plurality of output images 52_1, 52_2, . . . , an output image 52 in which each vertebra VB is identified and which is to be finally output.

As described above, in the second embodiment, the marker position display map generation unit 42 generates a marker position display map 51 of a marker MK corresponding to one vertebra VB among the plurality of contiguous vertebrae VB. The target object identification unit 43 outputs, from the SS model 133 for target object identification, the output image 52 in which each vertebra VB is identified. Therefore, although the processing time is longer than that in the first embodiment, each vertebra VB can be identified with higher accuracy.

As in the first embodiment, the markers MK may be attached to all the vertebrae VB appearing in the tomographic image 15 at once, or attaching a marker MK to one vertebra VB and identifying the one vertebra VB may be repeated.

Third Embodiment

Figure 22:
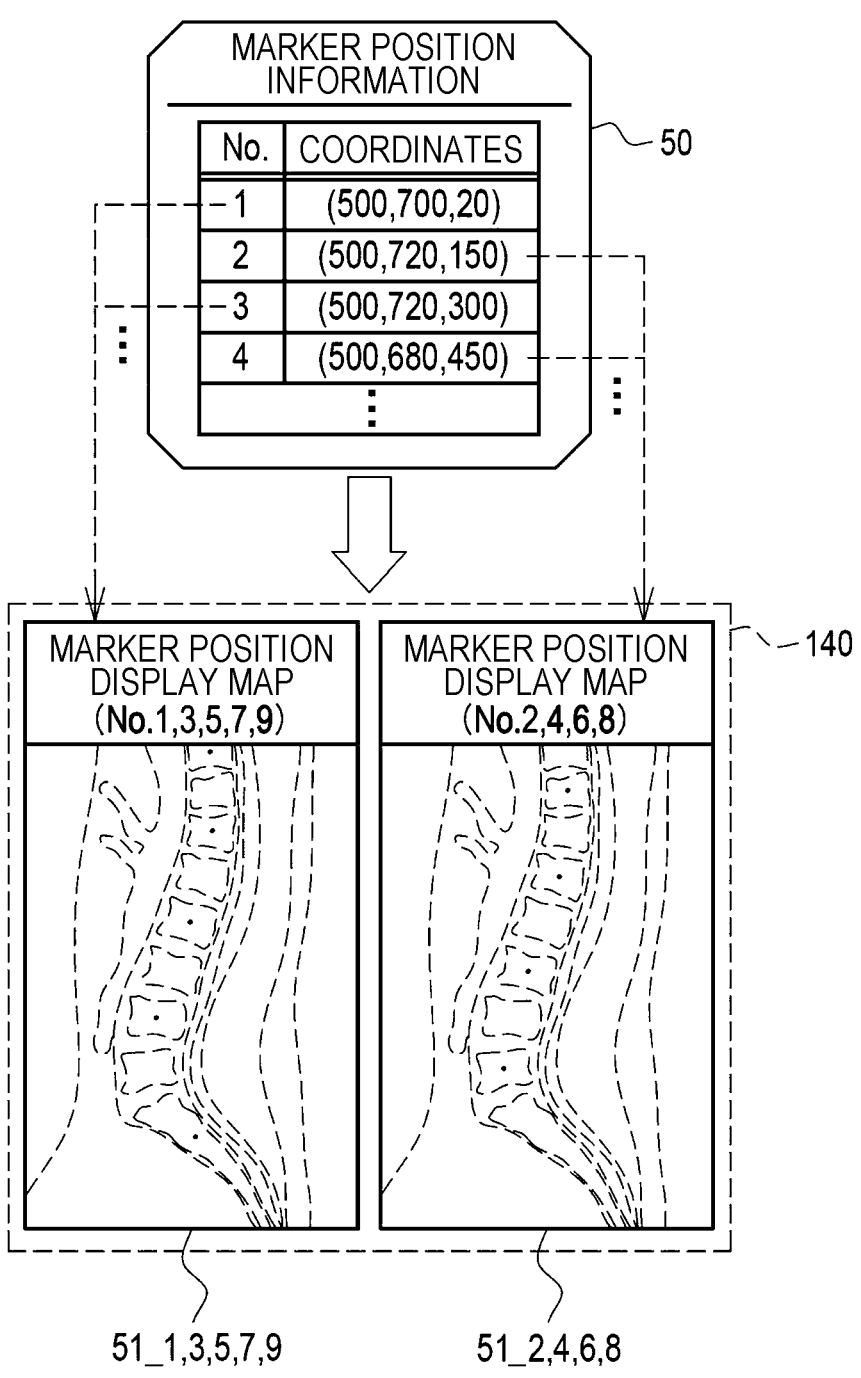
FIG. 22 is a diagram illustrating a state in which a marker position display map of markers corresponding to vertebrae arranged to face each other with one vertebra interposed therebetween among the plurality of contiguous vertebrae is generated.
Figure 23:
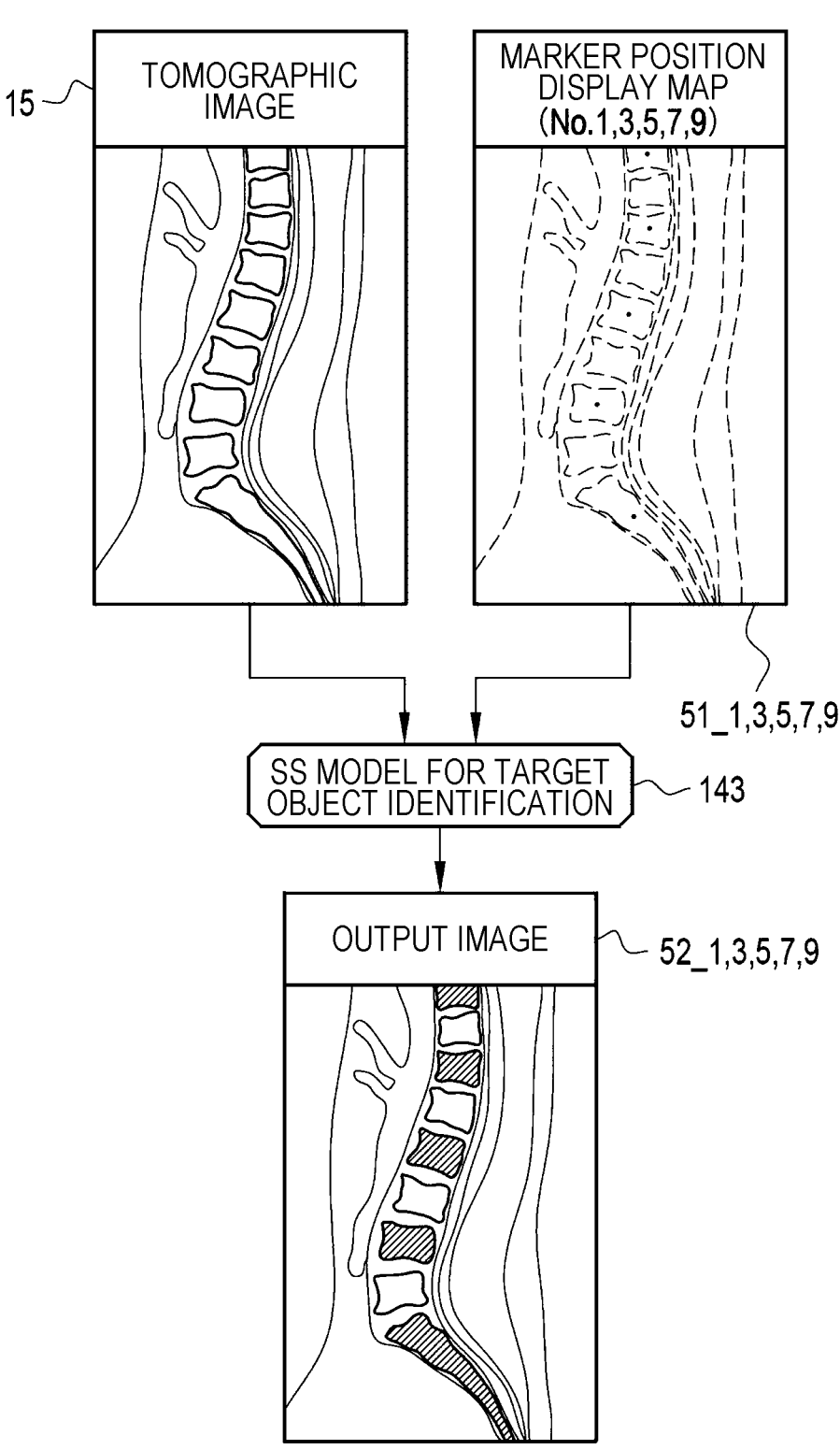
FIG. 23 is a diagram illustrating a state in which a tomographic image and a marker position display map of markers corresponding to vertebrae arranged to face each other with one vertebra interposed therebetween are input to a semantic segmentation model for target object identification, and an output image in which the vertebrae arranged to face each other with one vertebra interposed therebetween are identified is output from the semantic segmentation model for target object identification.
Figure 24:
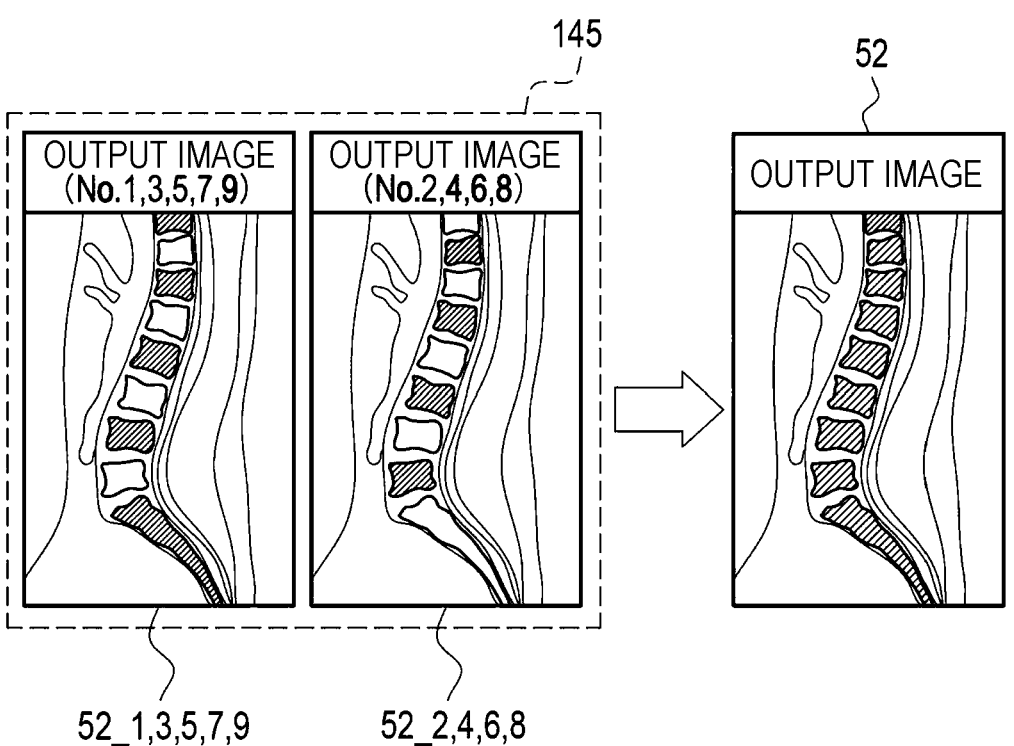
FIG. 24 is a diagram illustrating a state in which an output image in which each vertebra is identified is generated from an output image in which vertebrae arranged to face each other with one vertebra interposed therebetween are identified.

Instead of the above-described first embodiment in which the marker position display map 51 of the markers MK corresponding to all of the plurality of contiguous vertebrae VB is generated and the above-described second embodiment in which the marker position display map 51 of the marker MK corresponding to one vertebra VB among the plurality of contiguous vertebrae VB is generated, a third embodiment illustrated in FIGS. 22 to 24 may be adopted.

As an example, as illustrated in FIG. 22, the marker position display map generation unit 42 generates a marker position display map group 140 based on the marker position information 50. The marker position display map group 140 includes a marker position display map 51_1, 3, 5, 7, 9 indicating the positions of the markers MK attached to the Nos. 1, 3, 5, 7, and 9 vertebrae VB and a marker position display map 51_2, 4, 6, 8 indicating the positions of the markers MK attached to the Nos. 2, 4, 6, and 8 vertebrae VB. That is, in the present embodiment, the marker position display map generation unit 42 generates a marker position display map 51 of markers MK corresponding to vertebrae VB arranged to face each other with one vertebra VB interposed therebetween among the plurality of contiguous vertebrae VB.

For example, as illustrated in FIG. 23, the tomographic image 15 and one of the two marker position display maps 51 forming the marker position display map group 140 are input to an SS model 143 for target object identification according to the present embodiment. Further, the SS model 143 for target object identification outputs an output image 52 in which the vertebrae VB which are arranged to face each other with one vertebra VB interposed therebetween and to which the markers MK whose positions are represented in the marker position display map 51 are attached are identified. FIG. 23 illustrates a state in which the marker position display map 51_1, 3, 5, 7, 9 indicating the positions of the markers MK attached to the Nos. 1, 3, 5, 7, and 9 vertebrae VB is input to the SS model 143 for target object identification together with the tomographic image 15, and an output image 52_1, 3, 5, 7, 9 in which the Nos. 1, 3, 5, 7, and 9 vertebrae VB are identified is output from the SS model 143 for target object identification.

In a learning phase, a learning tomographic image 15L and a learning marker position display map 51L of markers MK corresponding to vertebrae VB arranged to face each other with one vertebra VB interposed therebetween are input to the SS model 143 for target object identification. Then, a loss of the SS model 143 for target object identification is calculated on the basis of a learning output image 52L output from the SS model 143 for target object identification and an annotation image in which the vertebrae VB to which the markers MK are attached and which are arranged to face each other with one vertebra VB interposed therebetween are annotated. Alternatively, similar to the SS model 133 for target object identification according to the second embodiment, the learning tomographic image 15L and the learning marker position display map 51L of the marker MK corresponding to one vertebra VB are input to the SS model 143 for target object identification. Then, a loss of the SS model 143 for target object identification is calculated on the basis of a learning output image 52L output from the SS model 143 for target object identification and an annotation image in which the one vertebra VB to which the marker MK is attached is annotated.

By repeating the processing illustrated in FIG. 23 on the marker position display map 51_2, 4, 6, 8, for example, an output image group 145 illustrated in FIG. 24 is obtained. The output image group 145 includes the output image 52_1, 3, 5, 7, 9 in which the Nos. 1, 3, 5, 7, and 9 vertebrae VB are identified and an output image 52_2, 4, 6, 8 in which the Nos. 2, 4, 6, and 8 vertebrae VB are identified. From these two output images 52_1, 3, 5, 7, 9 and 52_2, 4, 6, 8, the target object identification unit 43 generates an output image 52 in which each vertebra VB is identified and which is to be finally output.

In this manner, in the third embodiment, the marker position display map generation unit 42 generates a marker position display map 51 of markers MK corresponding to vertebrae VB arranged to face each other with one vertebra VB interposed therebetween among the plurality of contiguous vertebrae VB. The target object identification unit 43 outputs, from the SS model 143 for target object identification, an output image 52 in which the vertebrae VB arranged to face each other with one vertebra VB interposed therebetween are identified. Therefore, each vertebra VB can be identified with high accuracy in a processing time shorter than that in the second embodiment.

As in the first embodiment, the markers MK may be attached to all the vertebrae VB appearing in the tomographic image 15 at once, or the identification of the vertebra VB by attaching the markers MK to the Nos. 1, 3, 5, 7, and 9 vertebrae VB and the identification of the vertebra VB by attaching the markers MK to the Nos. 2, 4, 6, and 8 vertebrae VB may be separately performed.

The case where every other vertebra VB, such as the Nos. 1, 3, 5, 7, and 9 vertebrae VB, and the Nos. 2, 4, 6, and 8 vertebrae VB, is identified has been exemplified, but the present disclosure is not limited thereto. Every third vertebra VB, such as the Nos. 1, 4, and 7 vertebrae VB, the Nos. 2, 5, and 8 vertebrae VB, and Nos. 3, 6, and 9 vertebrae VB, may be identified. In addition, every fourth vertebra VB or every fifth vertebra VB may be identified. However, it is natural that, the processing time is longer than that in a case of every other one.

Fourth Embodiment

Although it has been described in each of the aforementioned embodiments that the doctor inputs the markers MK, the present disclosure is not limited thereto. As in a fourth embodiment illustrated in FIGS. 25 to 31, points in the vertebrae VB may be automatically extracted, and the extracted points may be received as markers MK.

Figure 25:
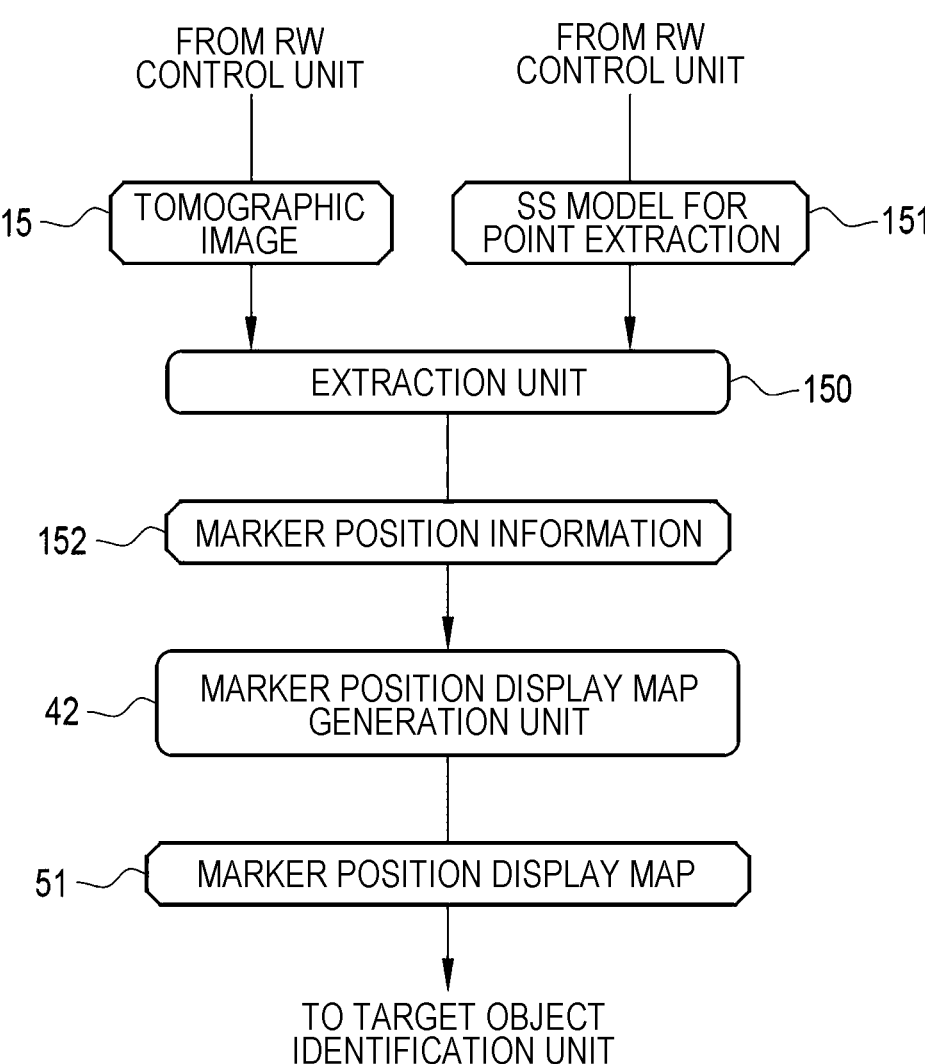
FIG. 25 is a block diagram illustrating processing units of a CPU according to a fourth embodiment.

As illustrated in FIG. 25 as an example, an extraction unit 150 is constructed in a CPU of a diagnosis support apparatus according to the present embodiment. The tomographic image 15 and an SS model 151 for point extraction are input to the extraction unit 150 from the RW control unit 40. The SS model 151 for point extraction is stored in the storage 20. The extraction unit 150 extracts a point within each vertebra VB appearing in the tomographic image 15 as a marker MK using the SS model 151 for point extraction. In this case, it is assumed that each of the center points CP (see FIG. 30) of the vertebral bodies is extracted as a point within each vertebra VB. The extraction unit 150 generates marker position information 152 indicating the positions of the center points CP of the vertebral bodies as the markers MK. The extraction unit 150 outputs the marker position information 152 to the marker position display map generation unit 42. The marker position display map generation unit 42 generates a marker position display map 51 on the basis of the marker position information 152 and outputs the marker position display map 51 to the target object identification unit 43. Since the subsequent processing is the same as that in each of the above-described embodiments, the description thereof will be omitted.

Figure 26:
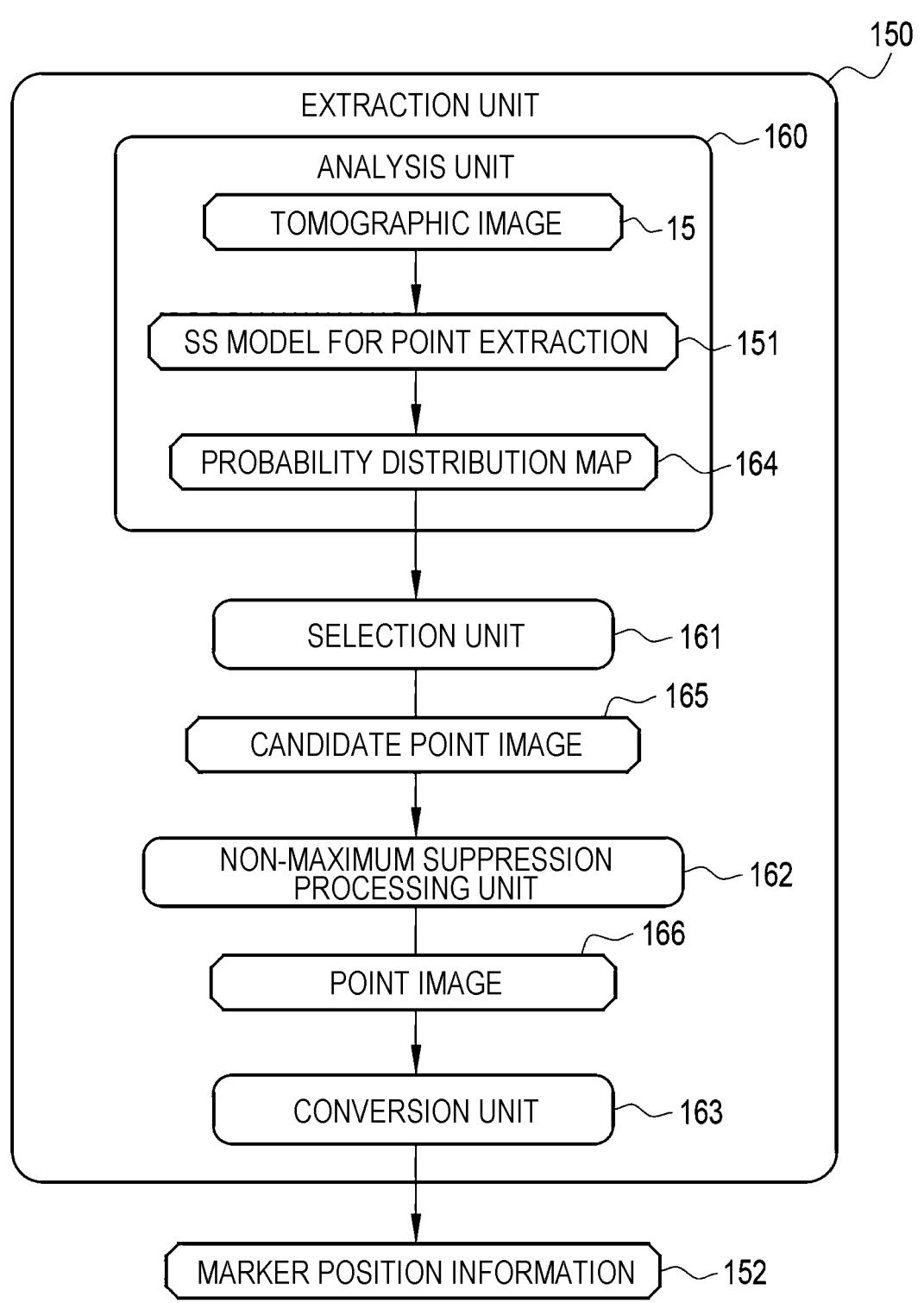
FIG. 26 is a diagram illustrating an extraction unit.

As an example, as illustrated in FIG. 26, the extraction unit 150 includes an analysis unit 160, a selection unit 161, a non-maximum suppression processing unit 162, and a conversion unit 163. The analysis unit 160 inputs the tomographic image 15 to the SS model 151 for point extraction, and outputs, from the SS model 151 for point extraction, a probability distribution map 164 indicating the presence probability of the center point CP of each vertebral body. The analysis unit 160 outputs the probability distribution map 164 to the selection unit 161.

Figure 27:
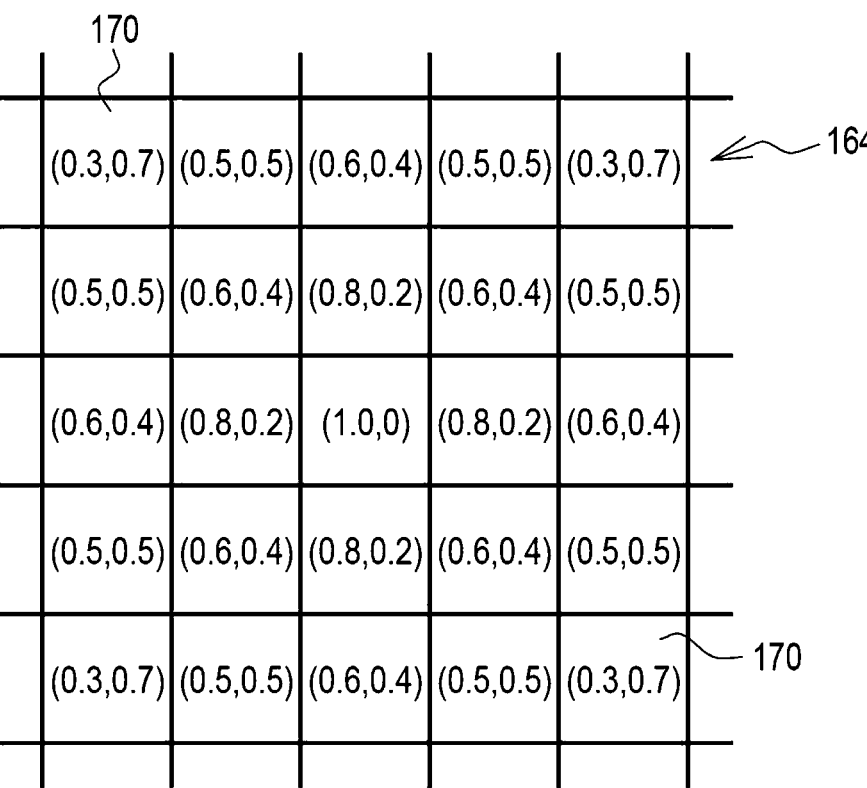
FIG. 27 is a diagram illustrating a probability distribution map.

As an example, as illustrated in FIG. 27, the probability distribution map 164 has elements 170 that correspond one-to-one with the pixels 86 of the tomographic image 15, and is data in which a pair of the presence probability and the absence probability of the center point CP of each vertebral body is registered as the element value of each element 170. For example, element values (1.0, 0) indicate that the presence probability of the center point CP of the vertebral body is 100% and the absence probability of the center point CP of the vertebral body is 0%.

Returning to FIG. 26, the selection unit 161 selects, as a candidate 200 (see FIG. 31) for each of the center points CP of the vertebral bodies, an element 170 of which the presence probability of the center point CP of the vertebral body is equal to or greater than a threshold value (for example, 0.9) in the probability distribution map 164. The selection unit 161 generates a candidate point image 165 (see also FIG. 31) representing the selected candidates 200, and outputs the generated candidate point image 165 to the non-maximum suppression processing unit 162. The candidate point image 165 is, for example, an image in which pixel values of pixels corresponding to the candidates 200 are 1 and pixel values of the other pixels are 0.

The non-maximum suppression processing unit 162 performs non-maximum suppression processing on each candidate 200 of the candidate point image 165, and as a result, generates a point image 166 (see also FIG. 31) representing the center points CP of the vertebral bodies. The point image 166 is, for example, an image in which the pixel values of pixels corresponding to the center points CP of the vertebral bodies are 1 and the pixel values of the other pixels are 0. That is, the point image 166 is nothing but an image representing the markers MK indicating the positions of the vertebrae VB in the tomographic image 15.

The non-maximum suppression processing unit 162 outputs the point image 166 to the conversion unit 163. By receiving the point image 166, the conversion unit 163 receives the input of the markers MK. The conversion unit 163 converts the point image 166 into marker position information 152.

Figure 28:
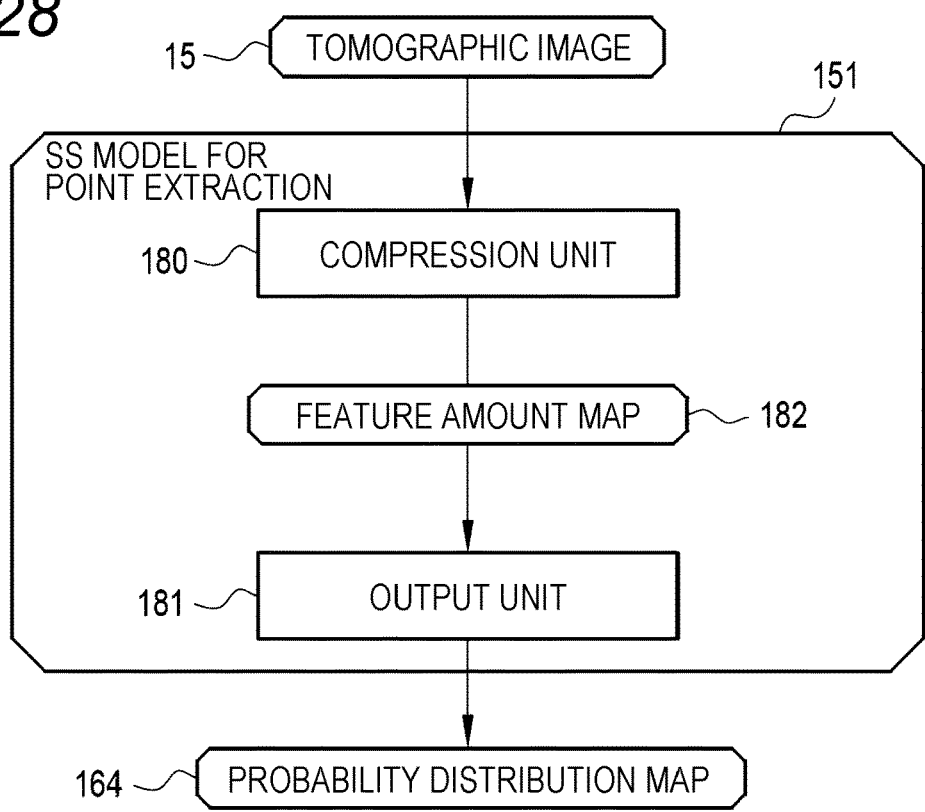
FIG. 28 is a diagram illustrating a semantic segmentation model for point extraction.

For example, as illustrated in FIG. 28, the SS model 151 for point extraction includes a compression unit 180 and an output unit 181, similar to the SS model 33 for target object identification. The tomographic image 15 is input to the compression unit 180. Similar to the compression unit 80 of the SS model 33 for target object identification, the compression unit 180 performs convolution processing, pooling processing, and the like on the tomographic image 15 to convert the tomographic image 15 into a feature amount map 182. The compression unit 180 sends the feature amount map 182 to the output unit 181. The output unit 181 outputs the probability distribution map 164 on the basis of the feature amount map 182.

Figure 29:
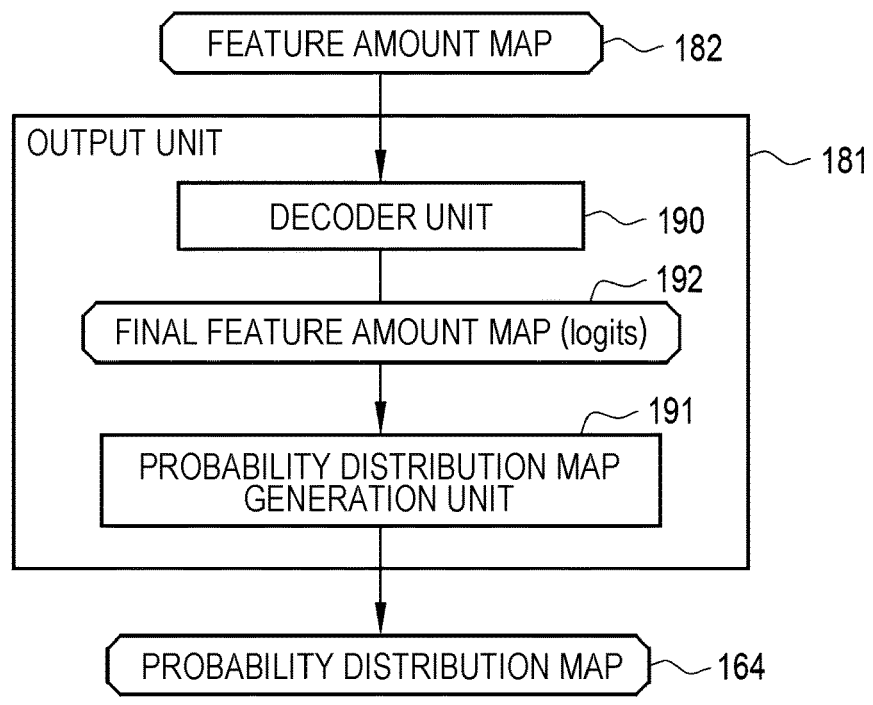
FIG. 29 is a diagram illustrating an output unit of the semantic segmentation model for point extraction.

As an example, as illustrated in FIG. 29, the output unit 181 includes a decoder unit 190 and a probability distribution map generation unit 191. Similar to the output unit 81 of the SS model 33 for target object identification, the decoder unit 190 performs upsampling processing, convolution processing, merge processing, and the like on the feature amount map 182 to generate a final feature amount map 192. The final feature amount map 192 is also referred to as logits and has elements in one-to-one correspondence with the pixels 86 of the tomographic image 15. Each element of the final feature amount map 192 has an element value related to the center point CP of each of the vertebral bodies to be extracted. For example, element values of elements in which the center points CP of the vertebral bodies are considered to be present are higher than the element values of the other elements. The decoder unit 190 outputs the final feature amount map 192 to the probability distribution map generation unit 191.

The probability distribution map generation unit 191 generates the probability distribution map 164 from the final feature amount map 192 using a known activation function.

For example, a case will be considered in which, in a certain element of the final feature amount map 192, an element value indicating that the certain element is the center point CP of a vertebral body is 2 and an element value indicating that the certain element is not the center point CP of a vertebral body is 1.5. In this case, the probability distribution map generation unit 191 uses, for example, a softmax function to calculate $e^2/(e^2+e^{1.5})$ and $e^{1.5}/(e^2+e^{1.5})$. Then, 0.62 ($\approx e^2/(e^2+e^{1.5})$) is derived as a probability that the center point CP of the vertebral body is present in the element, that is, a presence probability, and 0.38 ($\approx e^{1.5}/(e^2+e^{1.5})$) is derived as a probability (hereinafter referred to as an absence probability) that the center point CP of the vertebral body is not present in the element. Instead of using the softmax function, a sigmoid function may be used.

Figure 30:
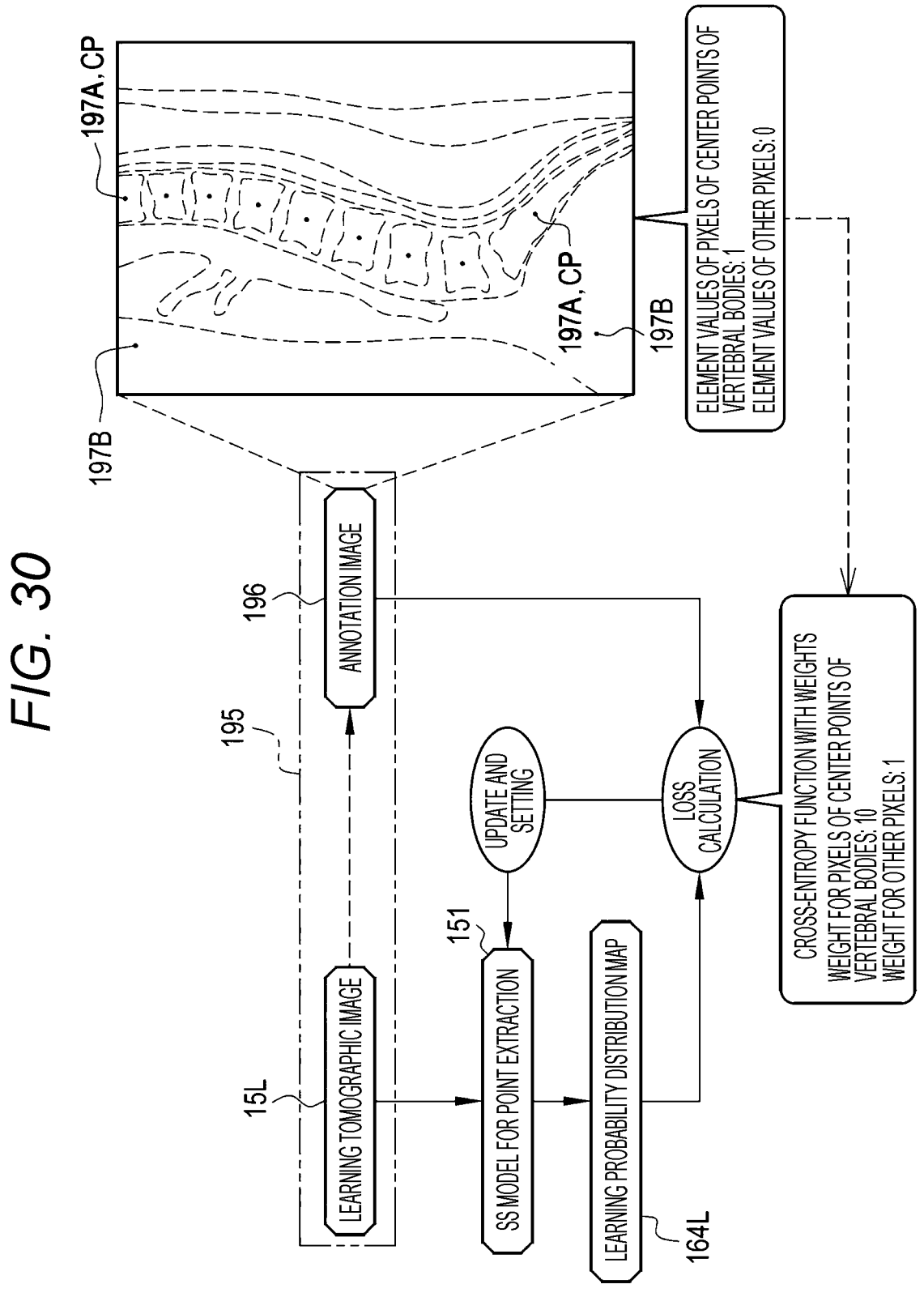
FIG. 30 is a diagram illustrating an overview of processing in a learning phase of the semantic segmentation model for point extraction.

As an example, as illustrated in FIG. 30, the SS model 151 for point extraction is trained by being given learning data 195 in the learning phase. The learning data 195 is a set of the learning tomographic image 15L and an annotation image 196 corresponding to the learning tomographic image 15L. The annotation image 196 is an image in which the center point CP of the vertebral body of each vertebra VB appearing in the learning tomographic image 15L is annotated. The annotation image 196 is an image in which the pixel values of pixels 197A corresponding to the center points CP of the vertebral bodies are set to 1 and the pixel values of the other pixels 197B are set to 0.

In a learning phase, the learning tomographic image 15L is input to the SS model 151 for point extraction. The SS model 151 for point extraction outputs a learning probability distribution map 164L to the learning tomographic image 15L. A loss of the SS model 151 for point extraction SS is calculated on the basis of the learning probability distribution map 164L and the annotation image 196. Then, various coefficients of the SS model 151 for point extraction are updated and set according to the result of the loss calculation, and the SS model 151 for point extraction is updated according to the update and setting of the coefficients.

In the calculation of the loss of the SS model 151 for point extraction, a cross-entropy function with weights is used. The cross-entropy function takes a relatively low value in a case where the presence probabilities of the center points CP of the vertebral bodies among the element values of the elements 170 of the learning probability distribution map 164L are relatively close to the pixel values of the annotation image 196. That is, in this case, the loss is estimated to be small. On the other hand, the cross-entropy function takes a relatively high value in a case where the presence probabilities of the center points CP of the vertebral bodies among the element values of the elements 170 of the learning probability distribution map 164L are relatively far from the pixel values of the annotation image 196. That is, in this case, the loss is estimated to be large.

The weight of the cross-entropy function is set to, for example, 10 for the pixels 197A corresponding to the center points CP of the vertebral bodies annotated in the annotation image 196, and is set to, for example, 1 for the other pixels 197B. Since the center points CP of the vertebral bodies are very small, the center points CP are buried and difficult to learn without any measures. However, since a larger weight is given to the pixels 197A corresponding to the center points CP of the vertebral bodies than that of the other pixels 197B, it is possible to perform learning with emphasis on the center points CP of the vertebral bodies.

In the learning phase of the SS model 151 for point extraction, the series of processes of inputting the learning tomographic image 15L to the SS model 151 for point extraction and outputting the learning probability distribution map 164L from the SS model 151 for point extraction, the loss calculation, the update and setting, and the update of the SS model 151 for point extraction are repeatedly performed while the learning data 195 is exchanged. The repetition of the series of processes is ended in a case where the accuracy of the prediction of the learning probability distribution map 164L for the annotation image 196 reaches a predetermined set level. The SS model 151 for point extraction of which the prediction accuracy reaches the set level is stored in the storage 20 and is used in the extraction unit 150. Regardless of the accuracy of the prediction of the learning probability distribution map 164L for the annotation image 196, the learning may be ended in a case where the series of processes is repeated a set number of times.

FIG. 31 illustrates an example of the non-maximum suppression processing by the non-maximum suppression processing unit 162. The candidate point image 165 is obtained by simply selecting, as the candidates 200, elements 170 whose presence probabilities in the probability distribution map 164 are equal to or higher than a threshold value. For this reason, not all of the candidates 200 are truly the center points CP of the vertebral bodies. Therefore, by performing the non-maximum suppression processing, the plurality of candidates 200 are narrowed down to the center points CP of the true vertebral bodies.

First, the non-maximum suppression processing unit 162 allocates a rectangular frame 201 to each candidate 200 of the candidate point image 165. The rectangular frames 201 have a preset size corresponding to the vertebrae VB, for example, a size larger than one vertebra VB. The centers of the rectangular frames 201 match the candidates 200.

Next, the non-maximum suppression processing unit 162 calculates intersection over union (IoU) of each of the rectangular frames 201 allocated to the candidates 200. IoU is a value obtained by dividing an area (area of overlap) where two rectangular frames 201 overlap by an area (area of union) where the two rectangular frames 201 are integrated. The non-maximum suppression processing unit 162 leaves one representative rectangular frame 201 out of two rectangular frames 201 of which IoU is equal to or greater than a threshold value (for example, 0.3), and deletes the other rectangular frame 201 together with the candidate 200. As a result, the two rectangular frames 201 of which IoU is equal to or greater than the threshold value are integrated into the one rectangular frame 201. By deleting the rectangular frame 201 overlapping the adjacent rectangular frame 201 with IoU equal to or greater than the threshold value and the candidate 200 in this manner, the point image 166 representing the center points CP of the vertebral bodies is finally obtained.

In this manner, in the fourth embodiment, the points in the vertebrae VB are automatically extracted and the extracted points are received as the markers MK. Therefore, the doctor can save the effort of inputting the markers MK. It is not necessary to display the second screen 70 illustrated in FIG. 5 on the display 17. The doctor only needs to select the analyze button 65 on the first screen 60.

The annotation image 196 is not limited to an image in which one pixel 197A indicating the center point CP of the vertebral body is annotated. The annotation image 196 may be an image in which a circular region constituted by several to several tens of pixels centered on the center point CP of the vertebral body is annotated. Further, the point to be extracted is not limited to the center point CP of the vertebral body. The point to be extracted may be the tip of the spinous process of the vertebral arch or may be the center of the vertebral foramen.

In each of the above-described embodiments, for example, the following various processors can be used as hardware structures of the processing units which perform the various processes, such as the RW control unit 40, the instruction reception unit 41, the marker position display map generation unit 42, the target object identification unit 43, the anatomical name assigning unit 44, the display control unit 45, the extraction unit 150, the analysis unit 160, the selection unit 161, the non-maximum suppression processing unit 162, and the conversion unit 163. As described above, in addition to the CPU 22 which is a general-purpose processor that executes software (operating program 30) to function as the various processing units, examples of the various processors include a programmable logic device (PLD) which is a processor having a circuit configuration which is changeable after a field-programmable gate array (FPGA) or the like is manufactured, and a dedicated electric circuit which is a processor having a circuit configuration designed as a dedicated circuit in order to perform specific processing, such as an application-specific integrated circuit (ASIC).

Each of the processing units may be configured by one of these various processors, or may be configured by a combination of two or more processors of the same type or different types (for example, a combination of a plurality of FPGAs and/or a combination of a CPU and an FPGA). In addition, a plurality of processing units may be configured by one processor.

As an example in which a plurality of processing units are configured by one processor, first, as represented by computers such as a client and a server, there is a form in which one processor is configured by a combination of one or more CPUs and software and this processor functions as the plurality of processing units. Second, as represented by a system on chip (SoC) or the like, there is a form in which a processor that implements the functions of the entire system including the plurality of processing units with one integrated circuit (IC) chip is used. As described above, the various processing units are configured using one or more of the various processors as a hardware structure.

Further, more specifically, an electric circuit (circuitry) in which circuit elements such as semiconductor elements are combined can be used as the hardware structure of the various processors.

The analysis target image is not limited to the tomographic image 15 obtained from the CT apparatus 10. For example, a tomographic image obtained from a magnetic resonance imaging (MRI) apparatus may be used. Further, the analysis target image is not limited to a three-dimensional image such as a tomographic image. For example, a two-dimensional image such as a simple radiographic image may be used.

The structure is not limited to the vertebrae VB. The structure may be a finger bone or the like. The analysis target image is not limited to a medical image. For this reason, the target objects are not limited to the structure of the body. For example, an image of a street may be used as the analysis target image, and the target objects may be human faces.

In the technology of the present disclosure, the above-described various embodiments and/or various modifications can be appropriately combined. Further, it is needless to say that the present disclosure is not limited to each of the above-described embodiments and various configurations can be adopted without departing from the scope of the present disclosure. Furthermore, the technology of the present disclosure extends to a storage medium that stores the program in a non-transitory manner, in addition to the program.

The details of the above descriptions and illustrations are detailed descriptions of the portions according to the technology of the present disclosure and are merely examples of the technology of the present disclosure. For example, the above description of the configurations, the functions, the actions, and the effects is an example of the configurations, functions, actions, and effects of the portions according to the technology of the present disclosure. Accordingly, it goes without saying that unnecessary portions may be removed, new elements may be added, or replacement may be made with respect to the details of the above descriptions and illustrations without departing from the scope of the technology of the present disclosure. In addition, in order to avoid complication and facilitate understanding of the portions according to the technology of the present disclosure, the description related to common technical knowledge or the like that does not need to be particularly described for enabling implementation of the technology of the present disclosure is omitted in the details of the above descriptions and illustrations.

In the present specification, "A and/or B" has the same meaning as "at least one of A or B". That is, "A and/or B" means that only A may be used, only B may be used, or a combination of A and B may be used. In addition, in the present specification, in a case where three or more matters are expressed by being connected with "and/or", the same concept as "A and/or B" is applied.

All the documents, patent applications, and technical standards described in this specification are herein incorporated by reference to the same extent as if each individual publication, patent application, or technical standard was specifically and individually indicated to be incorporated by reference.

What is claimed is:

1. An image processing apparatus comprising:
a processor; and
a memory connected to or incorporated in the processor,
wherein the processor acquires an analysis target image in which a plurality of contiguous target objects of the same type appear,
receives an input of a marker indicating positions of the target objects in the analysis target image,
generates a marker position display map indicating a position of the marker in the analysis target image,
inputs the analysis target image and the marker position display map to a semantic segmentation model, and
outputs, from the semantic segmentation model, an output image in which the target objects are identified,
wherein the processor combines the analysis target image and the marker position display map in a channel direction in the semantic segmentation model.

2. The image processing apparatus according to claim 1, wherein the processor generates the marker position display map of the marker corresponding to one of the plurality of contiguous target objects of the same type, and
outputs, from the semantic segmentation model, the output image in which the one target object is identified.

3. The image processing apparatus according to claim 1, wherein the processor generates the marker position display map of the marker corresponding to target objects arranged to face each other with at least one target object interposed therebetween among the contiguous target objects of the same type, and
outputs, from the semantic segmentation model, the output image in which the target objects arranged to face each other with at least one target object interposed therebetween are identified.

4. The image processing apparatus according to claim 1, wherein the processor generates the marker position display map of the marker corresponding to all of the plurality of contiguous target objects of the same type, and
in a case where the marker position display map is generated, the processor attaches a first label to a first target object out of first and second adjacent target objects among the plurality of contiguous target objects of the same type, attaches a second label different from the first label to the second target object, and outputs, from the semantic segmentation model, the output image in which the first target object is identified as a first class corresponding to the first label and the second target object is identified as a second class corresponding to the second label.

5. The image processing apparatus according to claim 1, wherein in a learning phase, a learning analysis target image and a learning marker position display map are input to the semantic segmentation model, and
the semantic segmentation model outputs a learning output image according to the learning analysis target image and the learning marker position display map, and is trained on the basis of comparison between the learning output image and an annotation image which is generated based on the learning analysis target image and in which the target objects to which the marker is attached are annotated.

6. The image processing apparatus according to claim 5, wherein the learning marker position display map is obtained by attaching a first label to a first target object out of first and second adjacent target objects among the plurality of contiguous target objects of the same type, attaching a second label different from the first label to the second target object.

7. The image processing apparatus according to claim 1, wherein the analysis target image is a medical image obtained by imaging an inside of a body of a patient, and
the target objects are a structure of the body.

8. The image processing apparatus according to claim 7, wherein the medical image is an image obtained by imaging a spine of the patient, and the structure is a vertebra forming the spine.

9. A method for operating an image processing apparatus, the method comprising:
acquiring an analysis target image in which a plurality of contiguous target objects of the same type appear;
receiving an input of a marker indicating positions of the target objects in the analysis target image;
generating a marker position display map indicating a position of the marker in the analysis target image;
inputting the analysis target image and the marker position display map to a semantic segmentation model, wherein the analysis target image and the marker position display map are combined in a channel direction in the semantic segmentation model; and
outputting, from the semantic segmentation model, an output image in which the target objects are identified.

10. A non-transitory computer-readable storage medium storing a program for operating an image processing apparatus, the program causing a computer to execute processing comprising:
acquiring an analysis target image in which a plurality of contiguous target objects of the same type appear;
receiving an input of a marker indicating positions of the target objects in the analysis target image;
generating a marker position display map indicating a position of the marker in the analysis target image;
inputting the analysis target image and the marker position display map to a semantic segmentation model, wherein the analysis target image and the marker position display map are combined in a channel direction in the semantic segmentation model; and
outputting, from the semantic segmentation model, an output image in which the target objects are identified.

\* \* \* \* \*